US011648306B2

(12) United States Patent
Dai et al.

(10) Patent No.: US 11,648,306 B2
(45) Date of Patent: May 16, 2023

(54) NON-INTEGRATIVE LISTERIA-BASED VACCINE AND METHOD FOR INDUCING ANTITUMOR IMMUNE RESPONSE

(71) Applicants: Suzhou RoyalTech Med CO., Ltd, Suzhou (CN); Shanghai RoyalTech Med CO., Ltd, Shanghai (CN)

(72) Inventors: Nan Dai, Suzhou (CN); Yonggang Zhao, Suzhou (CN)

(73) Assignees: Suzhou RoyalTech Med CO., Ltd, Suzhou (CN); Shanghai RoyalTech Med CO., Ltd, Shanghai (CN)

( * ) Notice: Subject to any disclaimer, the term of this patent is extended or adjusted under 35 U.S.C. 154(b) by 190 days.

(21) Appl. No.: 17/050,666

(22) PCT Filed: Apr. 23, 2019

(86) PCT No.: PCT/CN2019/083815
§ 371 (c)(1),
(2) Date: Oct. 26, 2020

(87) PCT Pub. No.: WO2019/206116
PCT Pub. Date: Oct. 31, 2019

(65) Prior Publication Data
US 2021/0308260 A1 Oct. 7, 2021

(30) Foreign Application Priority Data

Apr. 27, 2018 (CN) .................. 201810392619.X

(51) Int. Cl.
*A61K 39/385* (2006.01)
*A61P 35/00* (2006.01)
(Continued)

(52) U.S. Cl.
CPC ........ *A61K 39/385* (2013.01); *A61K 39/0011* (2013.01); *A61K 39/0208* (2013.01);
(Continued)

(58) Field of Classification Search
CPC .............. A61K 39/385; A61K 39/0208; A61K 39/0011; A61K 2039/6081;
(Continued)

(56) References Cited

U.S. PATENT DOCUMENTS 7,833,775 B2   11/2010   Dubensky, Jr. et al.
8,791,237 B2   7/2014    Paterson et al.

FOREIGN PATENT DOCUMENTS

CN   102076843   5/2011
CN   104955835   9/2015
(Continued)

OTHER PUBLICATIONS

International Preliminary Report on Patentability in Appl. No. PCT/CN2019/083815, dated Oct. 27, 2020, 5 pages.
(Continued)

*Primary Examiner* — Jana A Hines
(74) *Attorney, Agent, or Firm* — Fish & Richardson P.C.

(57) ABSTRACT

Disclosed are a non-integrative *Listeria*-based vaccine and a method for inducing antitumor immune response. In particular, the present disclosure provides a recombinant nucleic acid molecule, a recombinant plasmid or a recombinant expression vector comprising the recombinant nucleic acid molecule, a recombinant protein, and a recombinant *Listeria*. Also disclosed are a pharmaceutical composition and a vaccine comprising the above component, a method for slowly and continuously killing cells using the same, and a method for inducing immune response in a subject using the same.

15 Claims, 10 Drawing Sheets
Specification includes a Sequence Listing.

(51) Int. Cl.
*A61K 39/00* (2006.01)
*A61K 39/02* (2006.01)
*A61K 45/06* (2006.01)
*C07K 14/195* (2006.01)
*C07K 14/47* (2006.01)
*C07K 14/77* (2006.01)

(52) U.S. Cl.
CPC .............. *A61K 45/06* (2013.01); *A61P 35/00* (2018.01); *C07K 14/195* (2013.01); *C07K 14/4748* (2013.01); *C07K 14/77* (2013.01); *A61K 2039/522* (2013.01); *A61K 2039/523* (2013.01); *A61K 2039/585* (2013.01); *A61K 2039/6068* (2013.01); *A61K 2039/6081* (2013.01); *C07K 2319/55* (2013.01)

(58) Field of Classification Search
CPC ........ A61K 2039/585; A61K 2039/522; A61K 2039/523; A61K 2039/6068; A61K 45/06; C07K 14/195; C07K 14/77; C07K 14/4748; C07K 2319/55; A61P 35/00
See application file for complete search history.

(56) References Cited

FOREIGN PATENT DOCUMENTS

| CN | 106413745 | 2/2017 | |
|---|---|---|---|
| CN | 106459887 | 2/2017 | |
| CN | 107206060 | 9/2017 | |
| CN | 107427565 | 12/2017 | |
| CN | 107847611 | 3/2018 | |
| WO | WO 0009733 | 2/2000 | |
| WO | WO 2016/191545 | 12/2016 | |
| WO | WO 2017132547 | 8/2017 | |
| WO | WO-2017132547 A1 * | 8/2017 | ............. A61K 35/74 |

OTHER PUBLICATIONS

Roeske et al., "Delivery of Chicken Egg Ovalbumin to Dendritic Cells by Listeriolysin O-Secreting Vegetative Bacillus subtilis," J. Microbiol., Biotechnol., 2018, 28:1:122-135.

Azizoglu et al., "Mutant construction and integration vector-mediated gene complementation in listeria monocytogenes," Liseria Monocytogenes, 2014, pp. 201-211.

Brockstedt et al.," Promises and challenges for the development for listeria monocytogenes-based immunotherapies," Expert Rev. Vaccines, 2008, 7(7):1069-1084.

Hernandez-Flores et al., "Biological effects of listeriolysin O: implications for vaccination," BioMed Res. International, Feb. 2015, 9 pages.

Singh et al., "Cancer immunotherapy using recombinant listeria monocytogenes," Human Vaccines, 2011, 7(5): 497-505.

Xu et al., "Recombinant *E coli* LLO/OVA vaccination effectively inhibits murine melanoma metastasis to lung CD8T Cells immunity," Chinese J. of Cancer Res, 2009, 12(1):44-49 (English translation).

* cited by examiner

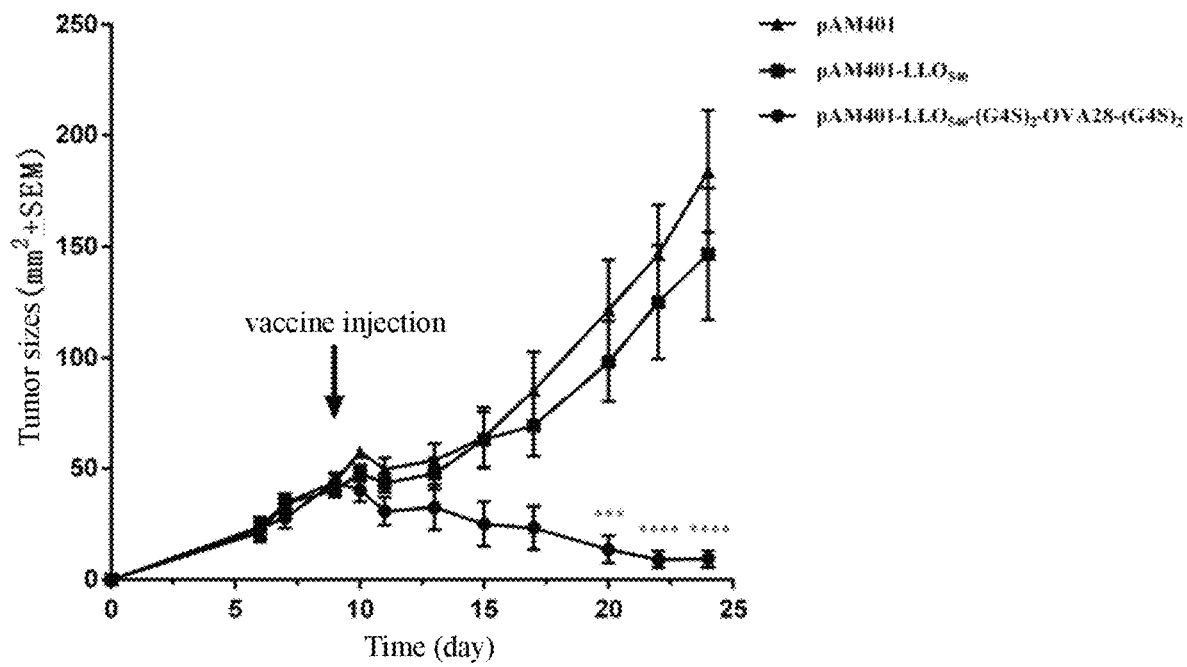

FIG. 5

| Tukey's multiple comparison test | the difference of mean | 95% confidence interval | significant difference | summary |
|---|---|---|---|---|
| Day 20 | | | | |
| pAM401 vs. pAM401-LLO540 | 23.26 | -45.39 ~ 91.90 | No | no difference |
| pAM401 vs. pAM401-LLO540-(G4S)2-OVA28-(G4S)2 | 107.8 | 39.18 ~ 176.5 | Yes | ** |
| pAM401-LLO540 vs. pAM401-LLO540-(G4S)2-OVA28-(G4S)2 | 84.58 | 18.62 ~ 150.5 | Yes | ** |
| Day 22 | | | | |
| pAM401 vs. pAM401-LLO540 | 21.44 | -47.21 ~ 90.99 | No | no difference |
| pAM401 vs. pAM401-LLO540-(G4S)2-OVA28-(G4S)2 | 137.3 | 68.70 ~ 206.0 | Yes | **** |
| pAM401-LLO540 vs. pAM401-LLO540-(G4S)2-OVA28-(G4S)2 | 115.9 | 48.95 ~ 181.9 | Yes | **** |
| Day 24 | | | | |
| pAM401 vs. pAM401-LLO540 | 37.21 | -31.44 ~ 105.9 | No | no difference |
| pAM401 vs. pAM401-LLO540-(G4S)2-OVA28-(G4S)2 | 174.5 | 105.9 ~ 243.2 | Yes | **** |
| pAM401-LLO540 vs. pAM401-LLO540-(G4S)2-OVA28-(G4S)2 | 137.3 | 71.39 ~ 203.3 | Yes | **** |

FIG. 6

NON-INTEGRATIVE LISTERIA-BASED VACCINE AND METHOD FOR INDUCING ANTITUMOR IMMUNE RESPONSE

CROSS-REFERENCE TO RELATED APPLICATIONS

This application is a National Stage application under 35 U.S.C. § 371 of International Application No. PCT/CN2019/083815, having an International Filing Date of Apr. 23, 2019, which claims priority to Chinese Application Serial No. 201810392619.X, filed on Apr. 27, 2018. The disclosure of the prior application is considered part of the disclosure of this application, and is incorporated in its entirety into this application.

TECHNICAL FIELD

The present disclosure mainly relates to the field of biotechnology. To be specific, the present disclosure provides a non-integrative attenuated *Listeria*-based vaccine against tumor or cancer, a method for improving the expression of an antitumor antigen peptide or an anticancer antigen peptide, and a method for enhancing antitumor immune response or anticancer immune response.

BACKGROUND

*Listeria monocytogenes* (Lm) is an important food-borne pathogenic bacterium, which widely exists in fresh or ready-to-eat foods and may cause serious listerellosis in elderly people, children, pregnant women and people suffering from immunosuppression. As a Gram-positive intracellular parasitic bacterium, *Listeria* is capable of surviving and reproducing in epithelial cells and phagocytes. In different stages of parasitism and reproduction, Lm has a plurality of virulence factors to facilitate its infection in the body, thereby exerting the pathogenic effects. Currently, a plurality of factors associated with the pathogenicity and virulence of Lm have been found, and most of these factors are surface proteins or secretory proteins. Virulence genes encoding these proteins (hly, plcA, plcB, mpl, actA, inlA and inlB) are mainly located on two virulence islands on the chromosome of the bacterium. Among them, Listeriolysion O (LLO) encoded by hly gene is a major virulence factor.

Acute infection with *Listeria* may induce strong and natural immune response mediated by TLR and cause the release of a large amount of pro-inflammatory factors. When *Listeria* is phagocytosed into a lysosome, the phagocytosed exogenous protein may also be directly presented by MHC Class II molecules, thereby activating the Lm-specific $CD4^+$ T cell immune response. In addition, *Listeria* is capable of escaping from lysosome via its characteristic Listeriolysion O (LLO) and entering into the cytoplasm to survive and reproduce. The expressed and secreted proteins are degraded by the proteases in host cells and the resulting polypeptide fragments may be presented by MHC Class I molecules, thereby activating $CD8^+$ T cell response, inducing stable Lm-specific CTL (cytotoxic T lymphocyte) response and providing protection against the subsequent bacterial infections. Of these, the two important virulence factors of Lm (i.e., LLO and P60) are both capable of inducing strong and specific $CD8^+$ T cell immune response. Therefore, such a combination that is capable of simultaneously inducing inflammatory response and activating MHC Class I and II antigen presentation pathways enables *Listeria* to become a vaccine vector with great application prospects.

In order to apply *Listeria* to the clinic, some highly attenuated Lm mutant strains have been developed into candidate strains for vaccine. Attenuation is carried out by knocking out its main virulence gene cluster prfA/plcA/hly (LLO)/mpl/actA and plcB, or attenuation is carried out by aiming at the most important virulence gene actA among the above virulence gene cluster. For example, the $LD_{50}$ of the Lm-ΔactA strain in which actA is knocked out is from $0.5 \times 10^8$ cfu to $1 \times 10^8$ cfu, and when compared to the $LD_{50}$ of the wild-type strain ($1 \times 10^4$ cfu), the Lm-ΔactA strain is proved to be highly attenuated. With the deepening of the research on attenuated Listerias, the development of tumor vaccines using an attenuated *Listeria* as a basic vector is also in full swing, tumor antigens delivered by attenuated Listerias include human papilloma virus HPV16 E7 antigen, melanoma antigen Mage-b, high-molecular-weight melanoma-associated antigen (HMW-MAA), prostate-specific antigen (PSA), mesothelin, tumor suppressor protein P53, antigen(s) in liver cancer, and the like [1]. Researches have shown that all mice immunized with the recombinant *Listeria*-based vaccine are capable of inducing specific CTL response and exhibiting good antitumor effects in mouse tumor models without causing significant side effects. Researches have shown that recombinant attenuated Listerias have excellent application prospects.

Across the world, current methods of constructing tumor vaccines by using attenuated Lm strains as vectors are mainly classified into two major categories. One of them is preparing a tumor vaccine by transforming a plasmid carrying the sequence of a tumor antigen peptide into an attenuated Lm strain, such as the most common balanced-lethal complementary system. That is, the multi-copy recombinant plasmid pGG-55 is transformed into LMΔprfA, prfA gene carried by pGG-55 forms a complementary system with the host bacterium, hly or actA promoter carried by pGG-55 promotes the realization of the fusion expression of LLO or ActA with exogenous antigen(s) [2]. However, in this method, the whole prfA virulence gene cluster is knocked out and then LLO functional genes are partially replenished, which may weaken the specific T cell immune response induced by the strain to some extent. The other kind of the aforementioned methods is preparing a tumor vaccine by integrating the sequence encoding a tumor antigen peptide into the genome of an attenuated LM strain, for example, conducting a site-specific integration of the sequence encoding a target antigen into the genome of LM using a temperature-sensitive plasmid pKSV7 by utilizing homologous recombination technology. This recombinant bacterium does not need the presence of antibiotic(s), and has obvious advantages in clinical application [3]. Alternatively, the sequence encoding an exogenous antigen may also be site-specifically integrated into a non-essential region (comK or Arg gene fragment of tRNA) of the genome of LM by using integrative vector pPL1 or pPL2, however, the presence of antibiotic(s) is required to be maintained in this method to screen the strain [4].

In summary, the *Listeria*-based vaccines in the prior art are mainly prepared by integrating antigen genes into chromosomes for expression via homologous recombination. Although such method may avoid the introduction of new resistance genes, there are disadvantages such as long construction period and complex integration and screening process. By contrast, although non-integrative *Listeria*-based vaccines has advantages in construction (such as shorter construction period and simple operation) as compared with integrative *Listeria*-based vaccines, there are problems in the expression level of antigen peptides and the stability of expression, thereby resulting in that the *Listeria*-based vaccines constructed by utilizing the above-mentioned methods have problems such as poor efficacy.

Since the above problems still exist in the existing technical solutions, there is a need to develop a novel *Listeria*-based vaccine with simple construction steps, less time consumption, high success rate of integration and greater practical application value.

PRIOR ART LITERATURES

[1] Singh R, Wallecha A. Cancer immunotherapy using recombinant *Listeria monocytogenes*: transition from bench to clinic. [J]. Human Vaccines, 2011, 7(5):497-505.

[2] Hernández-Flores K Vivanco-Cid H. Biological Effects of Listeriolysin O: Implications for Vaccination [J]. Biomed Research International, 2015, 2015(10).

[3] Azizoglu R O, Elhanafi D, Kathariou S. Mutant construction and integration vector-mediated gene complementation in *Listeria monocytogenes* [J]. Methods in Molecular Biology, 2014, 1157(1):201-11.

[4] Brockstedt D Dubensky T W. Promises and challenges for the development of *Listeria monocytogenes*-based immunotherapies [J]. Expert Review of Vaccines, 2008, 7(7):1069.

SUMMARY

Problems to be Solved by the Disclosure

In view of the defects existing in the prior art, a highly attenuated Lm strain is used as a vector and a plasmid that replicates independently is used to express an antigen gene in the present disclosure, thereby greatly reducing the cost and time consumed in vector construction and improving the expression efficiency of the vector to express the tumor antigen peptide by modifying the fragment of the secretory peptide.

Means for Solving the Problems

In one embodiment, the present disclosure relates to a recombinant nucleic acid molecule comprising an open reading frame encoding a recombinant polypeptide, the above-mentioned recombinant polypeptide comprises a heterologous antigen fused to a derived Listeriolysion O (LLO) polypeptide, the above-mentioned recombinant nucleic acid molecule further comprises a first promoter sequence; wherein the derived Listeriolysion O (LLO) polypeptide is a polypeptide as set forth in SEQ ID NO:2.

In one embodiment, the present disclosure relates to a recombinant nucleic acid molecule comprising an open reading frame encoding a recombinant polypeptide, the above-mentioned recombinant polypeptide comprises a heterologous antigen fused to a derived Listeriolysion O (LLO) polypeptide, the above-mentioned recombinant nucleic acid molecule further comprises a first promoter sequence; wherein the derived Listeriolysion O (LLO) polypeptide is selected from polypeptides that are obtained by substitution, repetition, deletion or addition of one or more amino acids in an amino acid sequence as set forth in SEQ ID NO:4 and have or partially have the activity of an Listeriolysion O (LLO) polypeptide as set forth in SEQ ID NO:2.

In one embodiment, the present disclosure relates to a recombinant nucleic acid molecule, wherein an amino acid sequence encoding the derived Listeriolysion O (LLO) polypeptide has at least 80% identity, preferably at least 90% identity, more preferably at least 95% identity and most preferably at least 97% identity with the amino acid sequence of the Listeriolysion O (LLO) polypeptide as set forth in SEQ ID NO: 2.

In one embodiment, the present disclosure relates to a recombinant nucleic acid molecule, wherein the above-mentioned polypeptide derived from LLO is a polypeptide as set forth in SEQ ID NO:4.

In one embodiment, the present disclosure relates to a recombinant nucleic acid molecule, wherein the above-mentioned heterologous antigen is selected from tumor antigens or non-tumor antigens; alternatively, the above-mentioned non-tumor antigens are selected from OVA or fragments having the function of OVA.

In one embodiment, the present disclosure relates to a recombinant nucleic acid molecule, wherein among the above-mentioned fragments having the function of OVA, the above-mentioned fragment has 2 amino acids to 40 amino acids in length; preferably, the above-mentioned fragment has 5 amino acids to 35 amino acids in length; and more preferably, the above-mentioned fragment has 8 amino acids to 28 amino acids in length.

In one embodiment, the present disclosure relates to a recombinant nucleic acid molecule, wherein an amino acid sequence of the above-mentioned OVA or an amino acid fragment having the function of OVA is selected from amino acid sequences comprising an amino acid sequence as set forth in SEQ ID NO:9 or SEQ ID NO:10; preferably, an nucleotide sequence encoding said OVA or the amino acid fragment having the function of OVA comprises a nucleotide sequence as set forth in SEQ ID NO:8.

In another embodiment, the present disclosure relates to a recombinant nucleic acid molecule further comprising a linking sequence, the above-mentioned linking sequence links a nucleotide sequence encoding the above-mentioned derived Listeriolysion O (LLO) polypeptide and a nucleotide sequence encoding the above-mentioned heterologous antigen; wherein the above-mentioned heterologous antigen is selected from tumor antigens or non-tumor antigens; alternatively, the above-mentioned non-tumor antigens are selected from OVA or fragments having the function of OVA.

In one embodiment, the present disclosure relates to a recombinant nucleic acid molecule, wherein the above-mentioned linking sequence comprises a nucleotide sequence encoding a sequence as set forth in SEQ ID NO:14; alternatively, the above-mentioned linking sequence comprises one, two, or three or more repetitions of the nucleotide sequence encoding the sequence as set forth in SEQ ID NO:14.

In one embodiment, the present disclosure relates to a recombinant nucleic acid molecule, wherein an amino acid sequence, encoded by a nucleotide sequence which is connected to the nucleotide sequence of the above-mentioned derived Listeriolysion O (LLO) polypeptide and comprises a linking sequence and the nucleotide sequence of the above-mentioned heterologous antigen, is as set forth in SEQ ID NO:15 or SEQ ID NO:16.

In one embodiment, the present disclosure relates to a recombinant nucleic acid molecule, wherein the above-mentioned promoter sequence is the sequence encoded by Phly gene; alternatively, the above-mentioned recombinant nucleic acid molecule further comprises a tag sequence for detection or a gene encoding a metabolite; preferably, the above-mentioned metabolite is selected from secondary metabolites.

In another embodiment, the present disclosure relates to a recombinant plasmid or a recombinant expression vector comprising the sequence of the above-mentioned recombinant nucleic acid molecule of the present disclosure.

In another embodiment, the present disclosure relates to a recombinant protein, which is encoded by the above-mentioned recombinant nucleic acid molecule of the present disclosure or produced by the above-mentioned recombinant plasmid or recombinant expression vector of the present disclosure.

In another embodiment, the present disclosure relates to a recombinant *Listeria*, which comprises the above-mentioned recombinant nucleic acid molecule of the present disclosure, or comprises the above-mentioned recombinant plasmid or recombinant expression vector of the present disclosure, or expresses the above-mentioned recombinant protein of the present disclosure.

In another embodiment, the present disclosure relates to a pharmaceutical composition comprising a therapeutically effective amount of the above-mentioned recombinant *Listeria* of the present disclosure.

In one embodiment, the present disclosure relates to a pharmaceutical composition, the above-mentioned pharmaceutical composition further comprises a second therapeutic agent; preferably, the above-mentioned second therapeutic agent is selected from a second anticancer agent; and more preferably, the above-mentioned second anticancer agent is selected from a second recombinant *Listeria*, radiotherapeutic agents, chemotherapeutic agents or immunotherapeutic agents.

In another embodiment, the present disclosure relates to a prophylactic or therapeutic vaccine, and this vaccine comprises a prophylactically or therapeutically effective amount of the above-mentioned recombinant *Listeria* of the present disclosure.

In one embodiment, the present disclosure relates to a prophylactic or therapeutic vaccine, which may further comprise an immunologic stimulant; alternatively, the above-mentioned immunologic stimulant is selected from adjuvants.

In another embodiment, the present disclosure relates to the use of the above-mentioned recombinant *Listeria*, the pharmaceutical composition or the vaccine in preparation of a drug for killing cells.

In one embodiment, the present disclosure relates to the above-mentioned use in preparation of a drug for killing cells, wherein the above-mentioned cells are contained in a patient.

In one embodiment, the present disclosure relates to the above-mentioned use in preparation of a drug for killing cells, the above-mentioned cells are selected from proliferative cells, neoplastic cells, precancerous cells or metastatic cells; preferably, the above-mentioned cells are selected from metastatic cells; and more preferably, the above-mentioned metastatic cells are selected from metastatic tumor cells.

In another embodiment, the present disclosure relates to the use of the above-mentioned pharmaceutical composition or the vaccine in preparation of a drug for treating a tumor patient.

In another embodiment, the present disclosure relates to a method for slowly and continuously killing cells, comprising contacting the above-mentioned cells with the recombinant *Listeria*, the pharmaceutical composition or the vaccine involved in the present disclosure.

In one embodiment, the present disclosure relates to a method for slowly and continuously killing cells, wherein the above-mentioned cells are contained in a patient.

In one embodiment, the present disclosure relates to a method for slowly and continuously killing cells, the above-mentioned cells are selected from proliferative cells, neoplastic cells, precancerous cells or metastatic cells; preferably, the above-mentioned cells are selected from metastatic cells; and more preferably, the above-mentioned metastatic cells are selected from metastatic tumor cells.

In one embodiment, the present disclosure relates to a method for slowly and continuously killing cells, wherein the recombinant *Listeria*, the pharmaceutical composition or the vaccine involved in the present disclosure is administered into a patient.

In one embodiment, the present disclosure relates to a method for slowly and continuously killing cells, wherein the recombinant *Listeria*, the pharmaceutical composition or the vaccine involved in the present disclosure may be administered via oral administration, intraperitoneal administration, intravenous administration, intraarterial administration, intramuscular administration, intradermal administration, subcutaneous administration, transdermal administration, nasal administration, transrectal administration, intratumoral injection, intratumoral indwelling, intraneurilemma injection, subarachnoid injection or systemic administration; alternatively, said systemic administration includes intravascular administration; preferably, said intravascular administration is selected from injection and perfusion.

In one embodiment, the present disclosure relates to a method for slowly and continuously killing cells, the above-mentioned method further comprises administering a second anticancer therapy; preferably, the above-mentioned second anticancer therapy may be a chemotherapy, a radiotherapy, an immunotherapy, a surgical therapy, or a combination of one or more of the above-mentioned therapies.

In another embodiment, the present disclosure relates to a method for inducing an immune response in a subject, wherein this method comprises administering the recombinant *Listeria*, the pharmaceutical composition or the vaccine involved in the present disclosure to the subject.

In another embodiment, the present disclosure relates to an isolated peptide consisting of an amino acid sequence, the above-mentioned amino acid sequence is selected from sequences that have a conservative mutation and comprise a sequence having at least 80% identity, preferably at least 90% identity, more preferably at least 95% identity and most preferably at least 97% identity with the amino acid sequence as set forth in SEQ ID NO: 4; or the above-mentioned amino acid sequence is the sequence as set forth in SEQ ID NO: 4.

In another embodiment, the present disclosure relates to a nucleotide sequence for encoding the above-mentioned isolated peptide.

Advantageous Effects of the Disclosure

The plasmid pAM401 adopted in the present disclosure is very stable during multiple passage processes of *Listeria*, neither loss nor mutation in the plasmid is found after 10 to 20 passages, and thus the plasmid may be safely used for the construction of a vaccine. The promoter Phly derived from *Listeria* LLO itself is selected and used for the expression and transcription of the antigen gene. This promoter is stable and highly efficient, and is capable of well initiating the transcription and translation of the constructed gene that encodes the heterologous antigen. Meanwhile, using the signal peptide sequence derived from LLO itself, the expressed protein is secreted into the exoplasm of the bacterium after the vaccine infects the cells and *Listeria* escapes from the lysosome, so as to induce cellular immune response. Alternatively, a tag for protein detection such as Flag-tag or His-tag is introduced into the plasmid for detecting the expression and secretion of protein.

Alternatively, the vector construction method adopted in the present disclosure and the vector obtained by the aforementioned method would not be influenced by the restriction site(s) on the heterologous antigen and have the advantages of convenient operation, high insertion efficiency and accurate insertion.

Alternatively, in terms of the design and optimization of the antigen peptide, the technical solution adopted in the present disclosure utilizes the codon preference of *E. coli* as the optimization criterion to satisfy the expression characteristics of *Listeria*, and the antigen peptide optimized and designed by this method is capable of being expressed in *Listeria* and has good stability. Meanwhile, by using the LLO signal peptide encoded by the sequence as set forth in SEQ ID NO:3 as a secretion signal, better expression of the secretory protein may be achieved as compared with the LLO signal peptide (28 amino acids in length) as set forth in SEQ ID NO:5, thereby enabling the heterologous antigen carried by *Listeria* to be efficiently secreted into host cells so as to fully activate the specific tumor immune response and achieve better therapeutic effects theoretically.

Alternatively, the technical solutions adopted in the present disclosure greatly improve the expression of the antigen peptide by the non-integrative *Listeria* tumor vaccine, thereby enabling the vaccine to have more prominent effects on inducing antitumor immune response. Illustratively, when the minimum effective dose of the vaccine is reduced to $10^4$ cfu, good efficacy and antitumor immune response are still achieved in animals. Therefore, the tumor vaccine constructed by this method greatly ensures safety while being effective. Illustratively, when compared with an integrative *Listeria*-based vaccine at a dose of $10^5$ cfu, the tumor vaccine prepared by the method adopted in the present disclosure has better effects in eliminating tumor and activating the specific immune response in vivo at a dose of $10^5$ cfu as compared with the integrative *Listeria*-based vaccine.

BRIEF DESCRIPTION OF THE DRAWINGS

FIG. 5 shows the therapeutic effects on EG7 tumor model after the injection of the vaccine.

FIG. 6 shows the results of the significant difference among the three groups on Day 20, 22 and 24 analyzed by t test.

Figure 1:
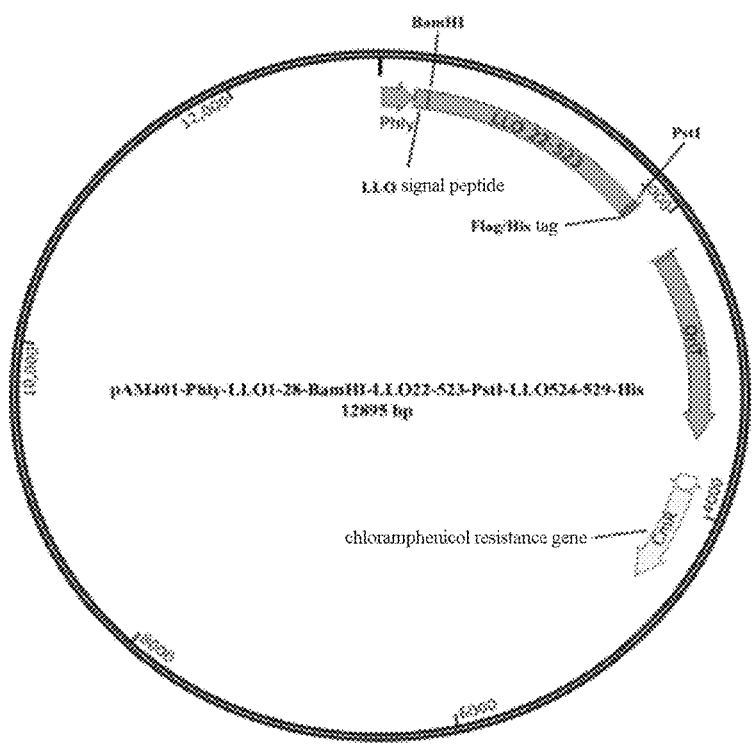
FIG. 1 shows the schematic diagram of the structure of the plasmid that is adopted and used to express the antigen gene in the present disclosure.

OVA$_{28}$-(G$_4$S)$_2$-His) strain as a template, and Lanes 3 and 4 show the PCR product using the plasmid DNA of LM 10403SΔactA (pAM401-hly-LLO$_{540}$-(G$_4$S)$_2$-OVA$_{28}$-(G$_4$S)$_2$-His) strain as a template.

STATEMENT REGARDING SEQUENCE LISTING

The Sequence Listing associated with this application is provided in text form in lieu of a paper copy, and is hereby incorporated by reference into the specification. The name of the text file containing the Sequence Listing is Amended_Sequence_Listing.txt. The text file is 16.6 KB, and was created and submitted electronically via EFS-Web on Jun. 28, 2021.

DETAILED DESCRIPTION

Definitions

When used in combination with the term "comprise" in claims and/or specification, the wording "a" or "an" may refer to "one", but may also refer to "one or more", "at least one" and "one or more than one".

As used in claims and specification, the wording "comprise", "have", "include" or "contain" means inclusive or open-ended, and does not exclude additional and unreferenced elements, method or steps.

Throughout the application document, the term "about" means that a value includes the standard deviation of the error of the device or method used to determine the value.

Although the definition of the term "or" as being an alternative only and as "and/or" are both supported by the disclosed content, the term "or" in claims means "and/or" unless it is explicitly indicated that the term "or" only means an alternative or the alternatives are mutually exclusive.

When used in claims or specification, the selected/alternative/preferred "numerical range" includes both the numerical endpoints at both ends of the range and all natural numbers covered by the range between said numerical endpoints with respect to the aforementioned numerical endpoints.

When used in claims and/or specification, the term "inhibition", "reduction", "prevention" or any variation of these terms includes any measurable reduction or complete inhibition for the purpose of achieving the desired results (for example, treatment of cancer). Desired results include but are not limited to the relief, reduction, slowing or eradication of a cancer, a hyperproliferative condition or a symptom related to a cancer, as well as the improved quality or extension of life.

The vaccination method in the present disclosure may be used for treating cancers in a mammal. The term "cancer" used in the present disclosure includes any cancer, including but not limited to melanoma, sarcoma, lymphoma, cancer (for example, brain cancer, breast cancer, liver cancer, gastric cancer, lung cancer, and colon cancer) and leukemia.

The term "mammal" in the present disclosure refers to human and non-human mammals.

The method of the present disclosure comprises administering to a mammal a vaccine comprising a tumor antigen to which the mammal has pre-existing immunity. The term "pre-existing immunity" used in the present disclosure is intended to include the immunity induced by vaccination with an antigen and the immunity naturally existing in a mammal.

The term "OVA" in the present disclosure refers to ovalbumin (also referred to as chicken ovalbumin), which consists of 386 amino acids and has a molecular weight of approximately 45 kD.

The term "Phly" in the present disclosure is the promoter of the gene encoding LLO (Listeriolysion O).

The term "vaccine" in the present disclosure refers to an immune formulation for preventing diseases prepared by methods such as artificially attenuating, inactivating or genetically modifying pathogenic microorganisms (such as bacteria) and the metabolites thereof.

The term "radiotherapeutic agent" in the present disclosure includes drugs that cause DNA damage. Radiotherapy has been widely used in the treatment of cancer and diseases, and includes those commonly referred to as γ-ray and X-ray and/or targeted delivery of radioisotopes to tumor cells.

The term "chemotherapeutic agent" in the present disclosure is a chemical compound useful for treating cancer. Classes of chemotherapeutic agents include but are not limited to: an alkylating agent, an antimetabolite, a kinase inhibitor, a spindle poison plant alkaloid, a cytotoxic/anti-tumor antibiotic, a topoisomerase inhibitor, a photosensitizer, an anti-estrogen, a selective estrogen receptor modulator, an anti-progesterone, an estrogen receptor downregulator, an estrogen receptor antagonist, a luteinizing hormone-releasing hormone agonist, anti-androgens, an aromatase inhibitor, an EGFR inhibitor, a VEGF inhibitor, an antisense oligonucleotide that inhibits the expression of gene(s) involved in abnormal cell proliferation or tumor growth. Chemotherapeutic agents that may be used in the treatment method of the present disclosure include a cell growth inhibitor and/or a cytotoxic agent.

The term "immunotherapeutic agent" in the present disclosure comprises an "immunomodulator" and an agent that facilitates or mediates an antigen presentation that increases a cell-mediated immune response. Among them, the "immunomodulator" comprises an immune checkpoint modulator. For example, immune checkpoint protein receptors and their ligands mediate the suppression of T cell-mediated cytotoxicity and are often expressed by tumors or expressed on anergic T cells in the tumor microenvironment, thus permitting the tumor to evade immune attack. Inhibitors of the activity of immunosuppressive checkpoint protein receptors and their ligands may overcome the immunosuppressive tumor environment, so as to permit cytotoxic T cell attack on tumor. Examples of immune checkpoint proteins include but are not limited to PD-1, PD-L1, PDL2, CTLA4, LAG3, TIM3, TIGIT and CD103. Modulation (including inhibition) of the activity of such protein may be accomplished by an immune checkpoint modulator, which may include, for example, an antibody, an aptamer, a small molecule, a soluble form of a checkpoint receptor protein and the like that target a checkpoint protein. PD-1-targeting inhibitors include the approved drug agents pembrolizumab and nivolumab, while ipilimumab is an approved CTLA-4 inhibitor. Antibodies specific for PD-L1, PD-L2, LAG3, TIM3, TIGIT and CD103 are known and/or commercially available, and may also be produced by those skilled in the art.

The term "substitution, repetition, deletion or addition of one or more amino acids" in the present disclosure includes a "conservative mutation". The term "conservative mutation" in the present disclosure refers to a conservative mutation capable of normally maintaining the function of the protein. A representative example of conservative mutations is conservative substitution. Conservative substitution refers to, for example, a mutation wherein substitution takes place mutually among Phe, Trp and Tyr in a case where the substitution site is an aromatic amino acid; a mutation wherein substitution takes place mutually among Leu, Ile and Val in a case where the substitution site is a hydrophobic amino acid; a mutation wherein substitution takes place mutually between Gln and Asn in a case where the substitution site is a polar amino acid; a mutation wherein substitution takes place mutually among Lys, Arg and His in a case where the substitution site is a basic amino acid; a mutation wherein substitution takes place mutually between Asp and Glu in a case where the substitution site is an acidic amino acid; and a mutation wherein substitution takes place mutually between Ser and Thr in a case where the substitution site is an amino acid having a hydroxyl group. As substitutions considered as conservative substitutions, there may be specifically exemplified substitution of Ser or Thr for Ala, substitution of Gln, His or Lys for Arg, substitution of Glu, Gln, Lys, His or Asp for Asn, substitution of Asn, Glu or Gln for Asp, substitution of Ser or Ala for Cys, substitution of Asn, Glu, Lys, His, Asp or Arg for Gln, substitution of Gly, Asn, Gln, Lys or Asp for Glu, substitution of Pro for Gly, substitution of Asn, Lys, Gln, Arg or Tyr for His, substitution of Leu, Met, Val or Phe for Ile, substitution of Ile, Met, Val or Phe for Leu, substitution of Asn, Glu, Gln, His or Arg for Lys, substitution of Ile, Leu, Val or Phe for Met, substitution of Trp, Tyr, Met, Ile or Leu for Phe, substitution of Thr or Ala for Ser, substitution of Ser or Ala for Thr, substitution of Phe or Tyr for Trp, substitution of His, Phe or Trp for Tyr, and substitution of Met, Ile or Leu for Val. In addition, the conservative mutations also include naturally occurring mutations which are attributed to the individual-derived gene differences, difference in strains, difference in species and the like.

As for the "conventional biological methods in this field" in the present disclosure, please refer to the corresponding methods described in the public publications such as "Current Protocols in Molecular Biology" published by Wiley, "Molecular Cloning: A Laboratory Manual" published by Cold Spring Harbor Laboratory.

Technical Solutions

In the embodiments of the present disclosure, the meanings of SEQ ID NOs in the nucleotide and amino acid sequence lists of the specification are as follows:

The sequence as set forth in SEQ ID NO:1 is the nucleotide sequence of the wild-type Listeriolysion O (LLO) ($LLO_{529}$).

The sequence as set forth in SEQ ID NO:2 is the amino acid sequence of the wild-type Listeriolysion O (LLO) ($LLO_{529}$).

The sequence as set forth in SEQ ID NO:3 is the nucleotide sequence of the recombinant Listeriolysion O (LLO) ($LLO_{540}$).

The sequence as set forth in SEQ ID NO:4 is the amino acid sequence of the recombinant Listeriolysion O (LLO) ($LLO_{540}$).

The sequence as set forth in SEQ ID NO:5 is the amino acid sequence of $LLO_{28}$. The sequence as set forth in SEQ ID NO:6 is the nucleotide sequence of $LLO_{28}$.

The sequence as set forth in SEQ ID NO:7 is an unoptimized nucleotide sequence of $OVA_{28}$.

The sequence as set forth in SEQ ID NO:8 is an optimized nucleotide sequence of $OVA_{28}$.

The sequence as set forth in SEQ ID NO:9 is an optimized amino acid sequence of $OVA_{28}$.

The sequence as set forth in SEQ ID NO:10 is the amino acid sequence of $OVA_8$.

The sequence as set forth in SEQ ID NO:11 is the nucleotide sequence of $OVA_8$.

The sequence as set forth in SEQ ID NO:12 is a nucleotide sequence of which the 5'-end is homologous to the 5'-end of its corresponding sequence.

The sequence as set forth in SEQ ID NO:13 is a nucleotide sequence of which the 3'-end is homologous to the 3'-end of its corresponding sequence.

The sequence as set forth in SEQ ID NO:14 is the amino acid sequence of the linking sequence.

The sequence as set forth in SEQ ID NO:15 is an amino acid sequence wherein the amino acid sequence of $OVA_8$ is linked to the linking sequence.

The sequence as set forth in SEQ ID NO:16 is an amino acid sequence wherein the amino acid sequence of $OVA_{28}$ is linked to the linking sequence.

In one embodiment of the present disclosure, said Listeriolysion O (LLO) polypeptide has at least 80%, 81%, 82%, 83%, 84%, 85%, 86%, 87%, 88%, 89%, 90%, 91%, 92%, 93%, 94%, 95%, 96%, 97%, 98%, 99%, 100% (including all ranges and percentages between these values) amino acid identity with the amino acid sequence as set forth in SEQ ID NO:1. The above-mentioned Listeriolysion O (LLO) polypeptides having a certain percentage of identity means that Listeriolysion O (LLO) polypeptides have conservative mutations capable of normally maintaining the function of the protein.

In one embodiment of the present disclosure, said Listeriolysion O (LLO) polypeptide is the polypeptide encoded by the sequence as set forth in SEQ ID NO:3.

In one embodiment of the present disclosure, in order to develop the pre-existing immunity, the method of the present disclosure comprises a step of vaccinating a mammal with a heterologous antigen suitable for inducing immune response against target cancer cells. In one example, said heterologous antigen is selected from tumor antigens. For example, the tumor antigen may be a tumor-associated antigen (TAA), such as a substance generated in tumor cells that trigger an immune response in a mammal. Examples of such antigens include oncofetal antigens (such as alpha-fetoprotein (AFP)) and carcinoembryonic antigen (CEA), surface glycoproteins (such as CA 125), oncogenes (such as Her2), melanoma-associated antigens (such as dopachrome tautomerase (DCT)), GP100 and MART1, cancer-testis antigens (such as MAGE protein and NY-ESO1), viral oncogenes (such as HPV E6 and E7), and proteins that are ectopically expressed in tumors and are usually limited to embryonic tissues or extra-embryonic tissues (such as PLAC1). As those skilled in the art should understand, antigen(s) may be selected according to the type of cancer to be treated by the method of the present disclosure since one or more antigens may be particularly suitable for treating certain cancers. For example, as for the treatment of melanoma, a melanoma-associated antigen such as DCT may be used. In another example, said heterologous antigen is selected from non-tumor antigens. For example, the non-tumor antigen is OVA.

An antigen itself may be administered, or preferably, an antigen may be administered via a vector such as an adenovirus (Ad) vector, a poxvirus vector or a retroviral vector, a plasmid, or an antigen-loaded antigen presenting cell such as a dendritic cell. The method of introducing an antigen into a vector is known to those skilled in the art. In general, the vector may be modified to express the antigen. In this regard, the widely accepted recombination technique is used to integrate the nucleic acid fragment encoding the selected antigen into the selected vector.

An antigen or a vaccine is administered to a mammal by any one of the several methods below, including but not limited to intravenous administration, intramuscular administration or intranasal administration. As those skilled in the art should understand, an antigen or a vector loaded with an antigen may be administered in a suitable vehicle (such as saline or other suitable buffer solutions). After vaccinated with the selected tumor antigen, the mammal produces an immune response within the interval of immune response, for example, the immune response may be produced within about 4 days and last for up to several months, several years or possibly the whole lifetime.

The method of the present disclosure may further include administering a second anticancer therapy, such as a second therapeutic virus. In other aspects, the second anticancer therapy is administering a chemotherapeutic agent, a radiotherapeutic agent or an immunotherapeutic agent, surgery, or the like.

In another aspect, said composition is a pharmaceutically acceptable composition. Said composition may further comprise a second anticancer agent, such as a chemotherapeutic agent, a radiotherapeutic agent or an immunotherapeutic agent.

Another embodiment of the present disclosure relates to a method for killing proliferative cells, this method comprises contacting these cells with the isolated vaccine composition of the present disclosure.

Another embodiment of the present disclosure relates to the treatment of cancer patients, comprising administering an effective amount of the vaccine composition of the present disclosure.

In certain aspects of the present disclosure, cells may be contained in a patient, and these cells may be proliferative cells, neoplastic cells, precancerous cells, or metastatic cells. The administration may be oral administration, intraperitoneal administration, intravenous administration, intraarterial administration, intramuscular administration, intradermal administration, subcutaneous administration, transdermal administration, nasal administration, or transrectal administration. In certain aspects, the composition is administered via systemic administration, especially via intravascular administration (including modes of administration such as injection and perfusion).

In one embodiment of the present disclosure, molecular cloning and vector construction methods are well known in the art, and any one of such methods may be used to generate constructs to provide elements such as double-strand break-inducing enzymes, artificial target sites, targeting vectors, cell proliferation factors or any other useful element. Vector construction is performed using standard molecular biology techniques. Any transformation method may be used, and vector construction and/or insert preparation may be modified accordingly.

In another embodiment of the present disclosure, the amino acid sequence of the heterologous antigen may be inserted into any site of the amino acid sequence of the wild-type Listeriolysion O (LLO) polypeptide encoded by the sequence as set forth in SEQ ID NO:1. Alternatively, the amino acid sequence of the heterologous antigen of the present disclosure may be inserted before the amino acid at position 514, 515, 516, 517, 518, 519, 520, 521, 522, 523, 524, 525, 526, 527, 528, or 529 in the amino acid sequence of the wild-type Listeriolysion O (LLO) polypeptide encoded by the sequence as set forth in SEQ ID NO:1. In one example, the amino acid sequence of the heterologous antigen of the present disclosure may be inserted between the amino acid at position 523 and the amino acid at position 524 in the amino acid sequence of the Listeriolysion O (LLO) polypeptide encoded by the sequence as set forth in SEQ ID NO: 1.

In another embodiment of the present disclosure, the amino acid sequence of the heterologous antigen may be inserted into any site of the amino acid sequence of the recombinant Listeriolysion O (LLO) polypeptide encoded by the sequence as set forth in SEQ ID NO:3. In one example, the amino acid sequence of the amino acids at positions 533 and 534 in the amino acid sequence of the recombinant Listeriolysion O (LLO) polypeptide encoded by the sequence as set forth in SEQ ID NO:3 may be replaced by the amino acid sequence encoding the heterologous antigen of the present disclosure.

In another embodiment of the present disclosure, the heterologous antigen is chicken ovalbumin (OVA). In one embodiment, the fragment recombined into the LLO polypeptide has 2 amino acids to 40 amino acids in length. In another embodiment, the fragment recombined into the LLO polypeptide has 5 amino acids to 35 amino acids in length. In another embodiment, the fragment recombined into the LLO polypeptide has 8 amino acids to 28 amino acids in length. In one embodiment, the sequence of the OVA fragment recombined into the LLO polypeptide is $OVA_{248-275}$ (i.e., the $OVA_{28}$ in the present disclosure). In another embodiment, the sequence of the OVA fragment recombined into the LLO polypeptide is $OVA_{258-265}$ (i.e., the $OVA_8$ in the present disclosure).

In one example, the present disclosure further comprises a connecting peptide recombined into a vector (vaccine). In one example, the sequence of said connecting peptide is a $(G_4S)_2$ sequence linked to fusion protein. In another embodiment, said fusion protein is linked to a connecting peptide at both ends; alternatively, the sequence of said connecting peptide is $(G_4S)_2$ sequence.

EXAMPLES

Other objects, features and advantages of the present disclosure will become apparent from the following detailed description. However, it should be understood that the detailed description and specific Examples (although representing the specific embodiments of the present disclosure) are given for explanatory purposes only, since various changes and modifications made within the spirit and scope of the present disclosure will become apparent to those skilled in the art after reading this detailed description.

Unless explicitly and specifically stated to the contrary, in the embodiments involved in all Examples of the present disclosure, the insertion sites of OVA are all located between the amino acid at position 523 and the amino acid at position 524 in the amino acid sequence of the wild-type LLO polypeptide that is encoded by the sequence as set forth in SEQ ID NO:1.

Unless otherwise specified, all reagents and raw materials adopted in the present disclosure are commercially available.

The main reagents used in the present disclosure are as follows: Plasmid Mini Extraction Kit (AXYGEN), Gel Extraction Kit (AXYGEN), Q5 PCR high-fidelity DNA polymerase (NEB), T4 DNA ligase (NEB), Ezmax for One-Step Cloning Kit (tolo bio), Human IFN-γ ELISPOT Set (BD), electroporator (Bio-Rad).

Example 1: Construction of the Plasmid for an Attenuated *Listeria*

An attenuated *Listeria* was used as the vector strain to prepare the vaccine in the present disclosure. Illustratively, the strain used for preparing the vaccine in the present disclosure was Lm 10403SΔactA (the construction method of the aforementioned strain could be exemplarily referred to the following literature: Shen H et. al., PNAS, 92(9): 3987-91, 1995). This strain lacked the actA gene, so that the microbe that infected the host cell was unable to spread to neighboring cells via its unique actin tail, thereby greatly reducing its toxicity and pathogenicity. As compared with the wild-type strain Lm 10403S ($LD_{50}$ was $1\times10^4$ cfu), Lm-ΔactA had an $LD_{50}$ of $0.5\times10^8$ cfu to $1\times10^8$ cfu and was proved to be highly attenuated. Meanwhile, this strain retained the complete ability to escape from the lysosome via LLO, enter the cytoplasm of the host cell and proliferate rapidly, and express the protein to activate the specific T cell immune response.

The basic structure of the plasmid used in the present disclosure to express the antigen gene was as follows.

(1) Basic sequence for maintaining the stable replication of the plasmid: illustratively, pAM401 was used as the basic sequence of the plasmid in the present disclosure.

(2) Promoter for the transcription of the antigen gene: illustratively, Phly (that is, the promoter of LLO on the virulence island of the chromosome of Lm) was used in the present disclosure.

(3) Signal peptide sequence for expressing and secreting the antigen protein outside of *Listeria*: illustratively, the signal peptide sequence of LLO, such as the sequence as set forth in $LLO_{1-28}$ and $LLO_{22-529}$, was used in the present disclosure, so as to increase the expression level of the heterologous protein.

(4) *Listeria* belonged to prokaryotic cells, however, it was generally required that the antigen peptide used in a tumor vaccine was derived from an eukaryotic cell, therefore, the corresponding codon optimization was required to enable the expression of a protein of an eukaryotic cell in a prokaryotic cell. Illustratively, an optimized sequence as set forth in SEQ ID NO:8 was used in the present disclosure.

(5) Tag sequence for detecting the secretory protein: illustratively, His-tag was used as the tag sequence in the present disclosure.

(6) Restriction site used for the insertion of the antigen peptide: illustratively, PstI was used as the restriction site in the present disclosure.

Illustratively, the method for constructing the plasmid pAM401-Phly-$LLO_{1-28}$-BamHI-$LLO_{22-523}$-PstI-$LLO_{524-529}$-His in the present disclosure was as follows. Based on the plasmid pAM401-Phly-$LLO_{1-28}$-BamHI and using BamHI as the restriction site, BamHI-$LLO_{22-529}$-His-BamHI sequence obtained by gene synthesis was constructed to this vector via enzyme digestion and enzyme ligation method to obtain pAM401-Phly-$LLO_{1-28}$-BamHI-$LLO_{22-529}$-His-BamHI. In order to add an insertion site for the exogenous gene, the upstream and downstream primers were designed at the selected site (i.e., $LLO_{523-524}$), and the PstI restriction site was inserted between $LLO_{523}$ and $LLO_{524}$ via PCR reaction.

The schematic diagram of the structure of the plasmid that was constructed by the above-mentioned method and used to express the antigen gene was as shown in FIG. 1.

Example 2: Construction of the Plasmid for an Attenuated *Listeria* Used for Vaccine The construction of the plasmid for an *Listeria*-based vaccine required the insertion of the antigen gene into a plasmid vector on which a restriction site had been designed, and the gene sequence of the target antigen was synthesized after the gene codon optimization was carried out by the company.

Alternatively, the codon optimization process of $OVA_{28}$ was as follows.

the nucleotide sequence of mouse $OVA_{28}$ before the optimization of the corresponding codons (SEQ ID NO:7):

GATGAAGTCTCAGGCCTTGAGCAGCTTGAGAGTATAATCAACTTTGAAA
AACTGACTGAATGGACCAGTTCTAATGTTATGGAA the nucleotide sequence of $OVA_{28}$ after the optimization of the corresponding codons (SEQ ID NO:8):

GATGAAGTGAGCGGCCTGGAGCAGCTGGAGAGCATTATCAACTTCGAAA
AACTGACCGAGTGGACCAGCAGCAATGTGATGGAA

The product was cloned to the PstI site on pAM401-phly-$LLO_{1-28}$-BamHI-$LLO_{22-523}$-PstI-$LLO_{524-540}$-His vector (simply referred to as PstI vector plasmid) by using the homologous recombination technology based on certain homologous sequences, the homologous sequences thereof were 5'-end homologous sequence (CCGAAATATAGTAATAAACTGCAG, SEQ ID NO:12) and 3'-end homologous sequence (CTGCAGGTAGA-TAATCCAATCGAA, SEQ ID NO:13).

The main steps were as follows.

20-μl PstI single restriction enzyme digestion system comprising PstI vector plasmid:

| | |
|---|---|
| PstI vector plasmid | 2 μg |
| PstI restriction enzyme | 2 μl |
| 10× NEB buffer solution 3.1 | 2 μl |
| deionized water | added until the total volume of the system reached 20 μl |

The reactants were reacted for 10 min in a water bath at 37° C.

The digested products were subjected to DNA extraction and purification, that is, the PstI vector was digested and linearized.

A 20-μl homologous recombination system comprised the following components (1) to (5):

(1) digested and linearized PstI vector (2) exogenous PCR fragment comprising homologous sequences at both ends (3) 5× buffer solution: 4 μl (4) reaction enzyme: 2 μl (5) ddH$_2$O: added until the total volume of the system reached 20 μl After the system was kept in a water bath at 37° C. for 30 minutes, *E. coli* competent cells were transformed and spread on a resistant plate, and a single clone was selected for sequencing and verification.

Example 3: Preparation of an Attenuated *Listeria*-Based Vaccine

The plasmid for the attenuated *Listeria* used for the vaccine that was verified as correct by sequencing was transformed into an attenuated *Listeria* strain by electrotransformation technology, and a single clone was selected for the subsequent verification of the expression of the plasmid.

The specific steps of the above-mentioned electrotransformation were as follows.

(1) Preparation of electro-transformation competent cells (i) *Listeria* cultured overnight was transferred into 100 to 250 ml of brain-heart infusion broth (BHI) medium at a ratio of 1:50 to 1:200 and was subjected to shaking culture at 37° C. until the $OD_{600}$ value reached 0.2 to 0.25.

(ii) Penicillin (PNG) was added thereto until the final concentration was 10 μg/ml, and the cultivation was continued for about two hours.

(iii) The mixture was subjected to high-speed centrifugation at 4° C. for 5 to 10 minutes to collect the microbes.

(iv) The microbes were re-suspended with 200 ml of 10% glycerin and washed twice.

(v) The microbes were re-suspended with 45 ml of 10% glycerin and a sterile solution of lysozyme was added thereto until the final concentration was 10 μg/ml. The resulting mixture was kept at ambient temperature for 20 minutes and mixed evenly by making it upside down every 10 minutes.

(vi) The mixture was subjected to high-speed centrifugation at 4° C. for 10 minutes to collect microbes, and then the microbes were washed once with 20 ml of 10% glycerin.

(vii) The microbes were re-suspended with 1 ml of 10% glycerin, dispensed into separate tubes (50 μl/tube), and stored at −80° C.

(2) Determination of the most suitable electrotransformation conditions (i) One tube of competent cells were taken, thawed, and placed on ice;

(ii) 1 μg of the plasmid to be transformed was added into the competent cells and the mixture was mixed evenly.

(iii) The above-mentioned mixed system was added into a pre-cooled electroporating cup (1 mm) and subjected to electric shock treatment. The conditions of the electric shock treatment were as follows. The electric field strength was 10 kV/cm, the resistance was 200 S2, the capacitance was 25 g, and the electric shock treatment lasted for 5 to 6 ms.

(iv) The resulting mixture was re-suspended with BHI medium and left to stand at ambient temperature for 1 hour.

(v) The microbes were spread on a resistant plate added with BHI and cultured overnight at 37° C. by placing the plate upside down, and a single colony was picked for verification.

The verified strains/colonies could be used as an attenuated *Listeria*-based vaccine.

Example 4: Improvement and Detection of the Expression of the Heterologous Protein by the Attenuated *Listeria*

*Listeria* was cultured overnight in BHI liquid medium at ambient temperature, the microbes were removed by centrifugation, a solution of TCA (trichloroacetic acid)/acetone was added to the supernatant, and the mixture was precipitated under a condition of −20° C. The precipitated protein was collected by ultra-high-speed centrifugation and washed twice with acetone to remove the residual TCA. A protein loading buffer containing 0.01 N NaOH was used to dissolve the precipitate. The sample was loaded after the protein was boiled and denatured, and a Western blot assay was conducted to determine the expression level of the protein via the tag attached to the protein. In one embodiment, the above-mentioned tag is selected from Flag-tag or His-tag.

Example 5: Effects of Culture Temperature on the Expression and Secretion of Protein Based on the plasmid obtained in Example 2, the corresponding plasmid adopted in Example 5 was obtained by conventional biological methods in this field. The attenuated Lm transfected with the plasmid pAM-hly-$LLO_{540}$-Flag was inoculated at a ratio of 1:100 into 10 ml of BHI (brain heart infusion broth) liquid medium containing chloramphenicol, and was respectively subjected to shaking culture for 12 h to 14 h in shakers at a constant temperature of 30° C. and 37° C. at 230 rpm. Subsequently, the bacteria solution was subjected to high-speed centrifugation for 10 min, the supernatant was taken and then a solution of TCA (trichloroacetic acid)/acetone was added therein, and the resultant was mixed evenly and was allowed to precipitate at −20° C. Subsequently, the protein was collected by ultra-high-speed centrifugation, the supernatant was removed, and the precipitate was washed twice with acetone. Finally, the precipitate was re-suspended in a protein loading buffer containing 0.01 N NaOH, denatured in a metal bath at 98° C. for 5 min, and stored in a refrigerator at −80° C. Western blot assay was conducted to detect the protein, and Anti-Flag-HRP antibody was used for detection.

Figure 2:
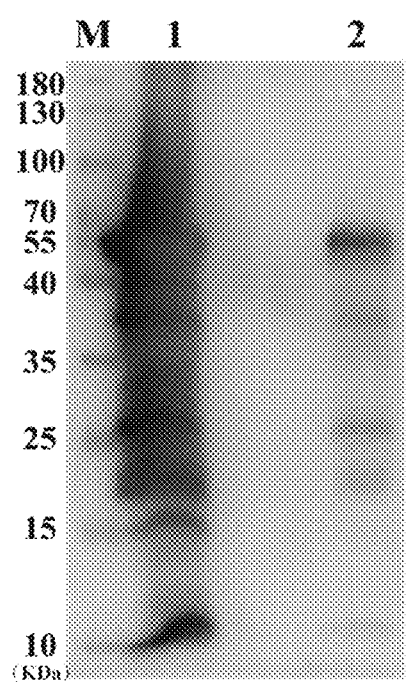
FIG. 2 shows the effects of the culture temperature on the expression and secretion of protein. Lane M: 180 KDa protein ladder as standard reference; Lane 1: the concentrated sample of the precipitated protein in the supernatant of Lm 10403 SΔactA (pAM401-hly-LLO$_{540}$-Flag) strain under culture conditions at 37° C.; Lane 2: the concentrated sample of the precipitated protein in the supernatant of Lm 10403 SΔactA (pAM401-hly-LLO$_{540}$-Flag) strain under culture conditions at 30° C.

The experimental results were as shown in FIG. 2. The experimental results indicated that the culture temperature had a relatively significant effect on protein expression and the expression level was significantly higher when the strain was cultured at 37° C. compared to the case where the strain was cultured at 30° C. Therefore, a culture temperature of 37° C. was adopted as the culture condition in the subsequent experiments of *Listeria*.

Example 6: Effects of the Full-Length LLO and the Conventional LLO Signal Peptide on the Expression of the Heterologous Protein Based on the plasmid obtained in Example 2, the corresponding plasmid adopted in Example 6 was obtained by conventional biological methods in this field. In order to further increase the expression level of the heterologous protein, the effects of $LLO_{28}$ signal peptide fragment (pAM401-hly-$LLO_{28}$-His) and the full-length $LLO_{540}$ fragment (pAM401-hly-$LLO_{540}$-His) comprising the signal peptide fragment on the subsequent expression of the heterologous protein were compared to determine whether the full-length LLO was more conducive to the expression of the heterologous protein as compared with the conventional LLO signal peptide.

The constructed pAM401-hly-$LLO_{28}$-His or pAM401-hly-$LLO_{540}$-His vector plasmid was electrotransformed into the attenuated Lm strain. The strain was inoculated at a ratio of 1:100 into 10 ml of BHI (brain heart infusion broth) liquid medium containing chloramphenicol, and was subjected to shaking culture for 12 h to 14 h in a shaker at a constant temperature of 37° C. at 230 rpm. Subsequently, the bacteria solution was subjected to high-speed centrifugation for 10 min, the supernatant was taken and then a solution of TCA (trichloroacetic acid)/acetone was added therein, and the resultant was mixed evenly and was allowed to precipitate at −20° C. Subsequently, the protein precipitate was collected by ultra-high-speed centrifugation, and the precipitate was washed twice with acetone. Finally, the precipitate was re-suspended in a protein loading buffer containing 0.01 N NaOH, denatured in a metal bath at 98° C. for 5 min, and stored in a refrigerator at −80° C. Western blot assay was conducted to detect the protein, and Anti-His-HRP antibody was used for detection.

Figure 3:
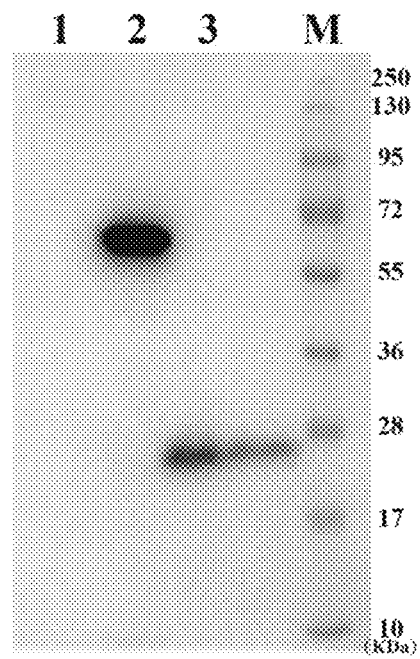
FIG. 3 shows the effects of the full-length LLO and the conventional LLO signal peptide on the expression of the heterologous protein. Lane M: 250 KDa protein ladder as standard reference; Lane 1: the concentrated sample of the precipitated protein in the supernatant of Lm 10403SΔactA strain; Lane 2: the concentrated sample of the precipitated protein in the supernatant of Lm 10403 SΔactA (pAM401-hly-LLO$_{540}$-His) strain; Lane 3: the concentrated sample of the precipitated protein in the supernatant of Lm 10403 SΔactA (pAM401-hly-LLO$_{28}$-His) strain.

The experimental results were as shown in FIG. 3. The results indicated that the expression level in $LLO_{540}$ experimental group was significantly higher than that in $LLO_{28}$ experimental group. Therefore, the full-length sequence of $LLO_{540}$ was adopted in subsequent experiments to increase the expression of the heterologous protein, and ideal expression could be achieved.

Example 7: Effects of Antigen Peptides of Different Sizes and the Presence or Absence of $G_4S$ Sequence on the Expression Vector Based on the plasmid obtained in Example 2, the corresponding plasmid adopted in Example 7 was obtained by conventional biological methods in this field. The attenuated Lm strains that were respectively constructed and comprised the plasmids pAM401-hly-$LLO_{540}$-$(G_4S)_2$-$OVA_{28}$-$(G_4S)_2$-His, pAM401-hly-$LLO_{540}$-$(G_4S)_2$-$OVA_8$-$(G_4S)_2$-His or pAM401-hly-$LLO_{540}$-$OVA_{28}$-His were inoculated at a ratio of 1:100 into 10 ml of BHI (brain heart infusion broth) liquid medium containing chloramphenicol, and were subjected to shaking culture for 12 h to 14 h in a shaker at a constant temperature of 37° C. at 230 rpm while using an attenuated Lm strain comprising the plasmid pAM401-hly-$LLO_{540}$-His as control. Subsequently, the bacteria solution was subjected to high-speed centrifugation for 10 min, the supernatant was taken and then a solution of TCA (trichloroacetic acid)/acetone was added therein, and the resultant was mixed evenly and was allowed to precipitate at −20° C. Subsequently, the protein precipitate was collected by ultra-high-speed centrifugation, and the precipitate was washed twice with acetone. Finally, the precipitate was re-suspended in a protein loading buffer containing 0.01 N NaOH, denatured in a metal bath at 98° C. for 5 min, and stored in a refrigerator at −80° C. Western blot assay was conducted to detect the protein, and Anti-His-HRP antibody was used for detection.

Figure 4:
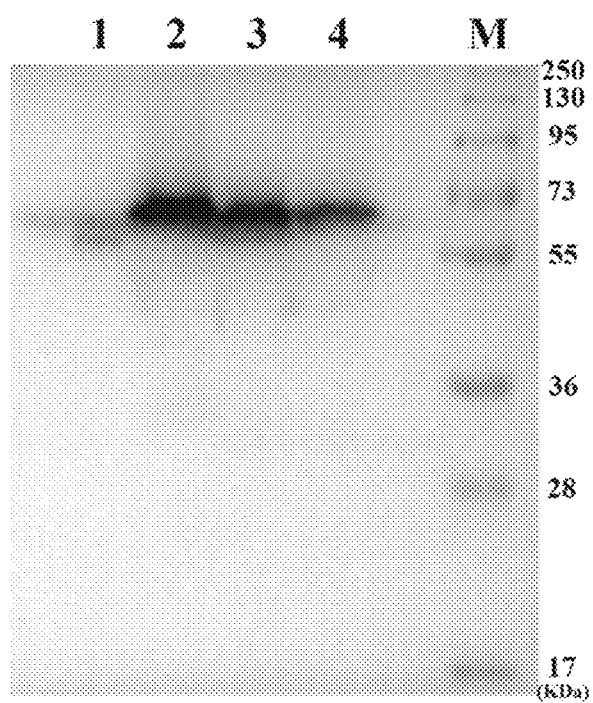
FIG. 4 shows the effects of antigen peptides of different sizes and the presence or absence of G4S sequence on the expression vector. Lane M: 250 KDa protein ladder as standard reference; Lane 1: the concentrated sample of the precipitated protein in the supernatant of Lm 10403SΔactA (pAM401-hly-LLO$_{540}$-His) strain; Lane 2: the concentrated sample of the precipitated protein in the supernatant of Lm 10403 SΔactA (pAM401-hly-LLO$_{540}$-(G$_4$S)$_2$-OVA$_{28}$-(G$_4$S)$_2$-His) strain; Lane 3: the concentrated sample of the precipitated protein in the supernatant of Lm 10403 SΔactA (pAM401-hly-LLO$_{540}$-(G$_4$S)$_2$-OVA$_8$-(G$_4$S)$_2$-His) strain; Lane 4: the concentrated sample of the precipitated protein in the supernatant of Lm 10403 SΔactA (pAM401-hly-LLO$_{540}$-OVA$_{28}$-His) strain.

The experimental results were as shown in FIG. 4. The results indicated that the attenuated Lm strains comprising $(G_4S)_2$-$OVA_{28}$-$(G_4S)_2$ sequence, $(G_4S)_2$-$OVA_8$-$(G_4S)_2$ sequence or $OVA_{28}$ sequence all showed relatively high expression level, the inclusion of $(G_4S)_2$ sequence did not affect the expression of the antigen peptide and resulted in relatively higher expression level of protein. Meanwhile, OVA antigen peptides of different sizes had little effect on expression and all resulted in relatively high expression level. The above results indicated that this experimental system was applicable to the secretion and expression of the exogenous antigen peptide. In one embodiment of the present disclosure, $(G_4S)_2$ could be used as the connecting peptide.

Example 8: Subcutaneously Inoculating Mice with EG7-OVA Tumor Cells to Generate Tumor, Treating the Mice with the Tumor Vaccine, and Testing the Antitumor Effects Based on the plasmid obtained in Example 2, the corresponding plasmid adopted in Example 8 was obtained by conventional biological methods in this field. Mice were inoculated subcutaneously with EG7-OVA tumor cells, and tumor sizes were measured from the 6th day after inoculation. The experimental mice were divided into three groups (pAM401 control group, pAM401-$LLO_{540}$ control group, pAM401-$LLO_{540}$-$(G_4S)_2$-$OVA_{28}$-$(G_4S)_2$ experimental group). On Day 9, the mice in pAM401 group, pAM401-$LLO_{540}$ group and pAM401-$LLO_{540}$-$(G_4S)_2$-$OVA_{28}$-$(G_4S)_2$ group were intravenously injected with the tumor vaccine via tail vein, the injection dose was $10^7$ cfu (the half lethal dose $LD_{50}$ of attenuated *Listeria* Lm ΔactA in mice was $10^8$ cfu, therefore, one-tenth of the half lethal dose was selected as the highest injection dose), and the tumor sizes were tracked and measured continuously. Tumor sizes were tracked and measured for 24 days to obtain the tumor growth curve. Meanwhile, the data of the three groups on Day 20, 22 and 24 were analyzed by Tukey's multiple comparison test.

The results of the tumor growth curve were as shown in FIG. 5. It could be seen that, as compared with pAM401 group and pAM401-$LLO_{540}$ group, there was a significant tendency of tumor elimination in $OVA_{28}$ treatment group after the injection of the vaccine. The analysis results of T test were as shown in FIG. 6, indicating that the experimental group pAM401-$LLO_{540}$-$(G_4S)_2$-$OVA_{28}$ showed significant difference when compared with the control groups (pAM401 and pAM401-$LLO_{540}$) while there was no significant difference between pAM401-$LLO_{540}$ group and pAM401 group.

In view of the above-mentioned experimental results, it was possible to activate the immune system of the body by *Listeria* carrying the sequence encoding antigen peptide $OVA_{28}$, thereby inducing the antitumor response specific to EG7-OVA tumor. However, the $LLO_{540}$ expressed alone did not participate in the antitumor immune response caused by the antigen peptide.

Example 9: Detection of the Activation of the Specific Immune Response in Mice by Lm OVA Vaccine Via ELISPOT Assay Based on the plasmid obtained in Example 2, the corresponding plasmid adopted in Example 9 was obtained by conventional biological methods in this field. The experimental mice were divided into the following groups: pAM401 control group, pAM401-$LLO_{540}$ control group, pAM401-$LLO_{540}$-$(G_4S)_2$-$OVA_{28}$-$(G_4S)_2$ experimental group, and OT1 positive control group. OT1 transgenic mice had the intact gene encoding OVA-specific T-cell antigen receptor, and were therefore selected as the positive control. First, the mice in pAM401 group, pAM401-$LLO_{540}$ group and pAM401-$LLO_{540}$-$(G_4S)_2$-$OVA_{28}$-$(G_4S)_2$ group were intravenously injected with the tumor vaccine via tail vein. On the 6th day after vaccine injection, submandibular blood sampling was carried out and peripheral blood mononuclear cells were separated to conduct ELISPOT-related experiments. EDTA was added as an anticoagulant during the blood sampling process, then red blood cells were lysed by red blood cell lysis solution, and the resultant was washed twice with PBS and centrifuged at 400 g for 5 min to obtain peripheral blood mononuclear cells. Finally, the cells were respectively re-suspended in 100 μl of 1640 complete culture medium (containing 10% FBS and 1% Penicillin-Streptomycin) and the resultant was added into a pre-treated ELISPOT plate. Subsequently, peripheral blood mononuclear cells were stimulated to produce IFN-γ by adding OVA polypeptide to the ELISPOT plate, and finally, the number of spots was quantified by enzyme-linked immunosorbent assay to indicate the specific immune response of each group in response to OVA polypeptide (for specific protocol of ELISPOT assay, please refer to the specification of BD™ ELISPOT Mouse IFN-γ ELISPOT Set, product number: 551083).

Figure 7:
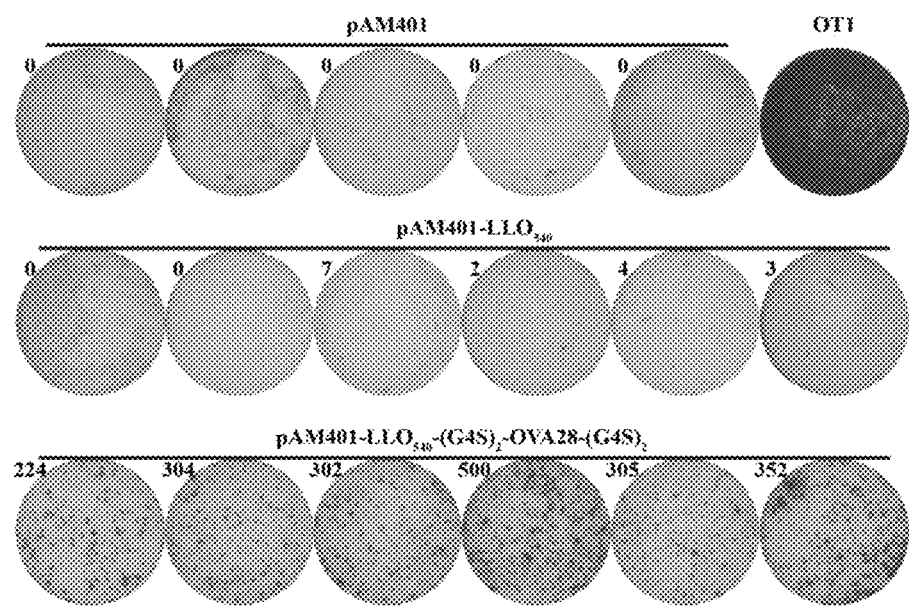
FIG. 7 shows the results of the functional test conducted by means of ELISPOT assay.

The experimental results were as shown in FIG. 7. The results indicated that OT1 positive control group showed obvious spots, indicating that there was no problem with the experimental operation. The number of spots in pAM401 control group and pAM401-$LLO_{540}$ control group were both within 10 spots, indicating that there was no obvious specific immune response. By contrast, all pAM401-LLO$_{540}$-(G$_4$S)$_2$-OVA$_{28}$-(G$_4$S)$_2$ experimental groups showed 200 or more spots and obvious ELISPOT response, indicating that the injected LM-OVA$_{28}$ tumor vaccine was capable of activating the tumor-specific immune response in mouse immune system, thus proving the functionality of the vaccine.

Example 10: Verifying the Specific Immune Response Induced by OVA$_{28}$ Tumor Vaccine in Mice by Tetramer Assay Based on the plasmid obtained in Example 2, the corresponding plasmid adopted in Example 10 was obtained by conventional biological methods in this field. The experimental mice were divided into the following groups: pAM401 control group, pAM401-LLO$_{540}$-(G$_4$S)$_2$-OVA$_{28}$-(G$_4$S)$_2$ experimental group, and OT1 positive control group. On the 7th day after the mice in pAM401 group and pAM401-LLO$_{540}$-(G$_4$S)$_2$-OVA$_{28}$-(G$_4$S)$_2$ group were respectively injected with the vaccine, submandibular blood sampling was carried out, OVA tetramer staining and the staining of CD8-PB and CD3-PE antibodies used in flow cytometry were conducted, and the detection was carried out by using a flow cytometer.

Figure 8:
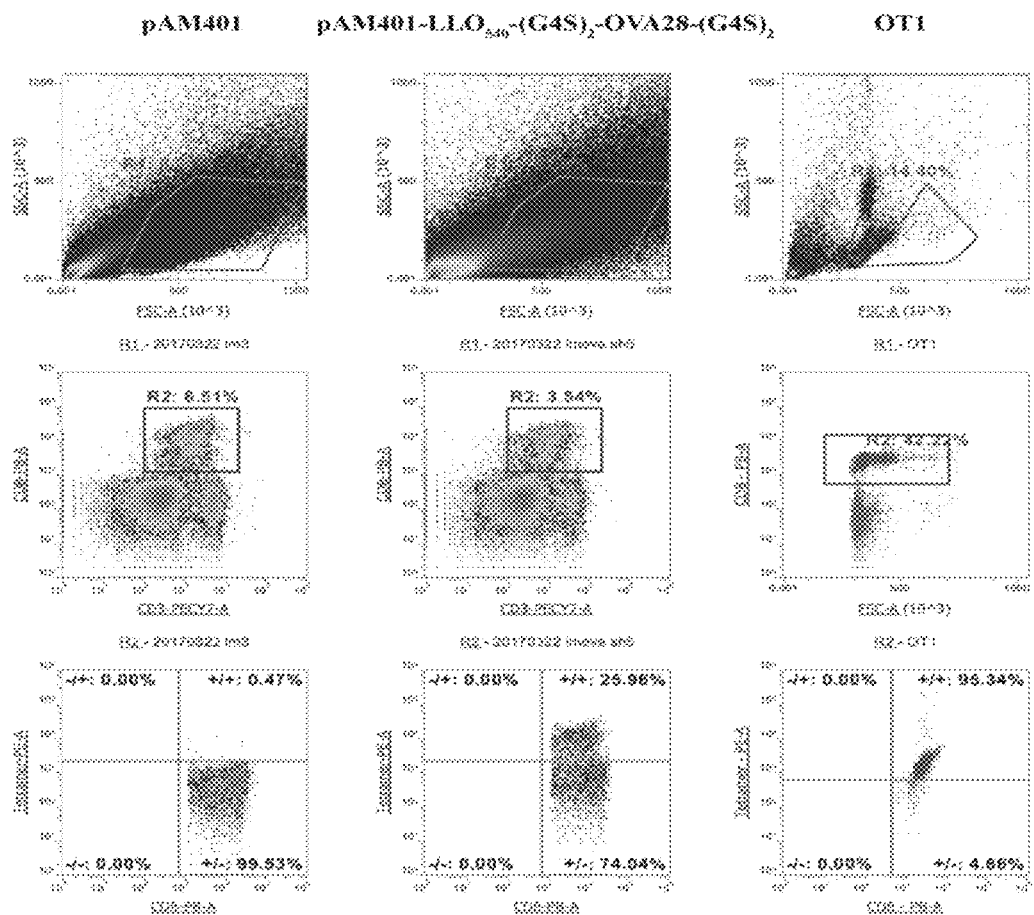
FIG. 8 shows the results of the functional test conducted by means of tetramer assay.

The experimental results were as shown in FIG. 8. It was found by flow cytometry that the proportion of CD8$^+$ T cells specifically recognized by OVA in OT1 positive control group was 95.34%, which conformed to the characteristics of OT1 and indicated that there was no problem with the experimental operation. The proportion of CD8$^+$ T cells specifically recognized by OVA in pAM401 control group was 0.45%, and the proportion of CD8$^+$ T cells specifically recognized by OVA in pAM401-LLO$_{540}$-(G$_4$S)$_2$-OVA$_{28}$-(G$_4$S)$_2$ experimental group was 25.96%, which was significantly higher than that of the control group. It indicated that the injection of Lm vaccine that highly expressed OVA$_{28}$ could activate the specific immune response in C57 mice, effectively increase the proportion of CD8$^+$ T cells specifically recognized by OVA and enhance OVA-specific tumor immune response.

Example 11: Determination of the Therapeutic Effects of B16-M30 Tumor Vaccine on Melanoma Based on the plasmid obtained in Example 2, the corresponding plasmid adopted in Example 11 was obtained by conventional biological methods in this field. First, tumor models were established by subcutaneously inoculating C57 mice with B16 cells. On the 7th day of the tumor growth, B16-M30 tumor vaccine was injected via the tail vein of mice. The experimental mice were divided into three groups: pAM401 control group, pAM401-LLO$_{540}$ control group, and pAM401-LLO$_{540}$-(G$_4$S)$_2$-B16-M30-(G$_4$S)$_2$ experimental group, and the injection dose of the vaccine was 1×10$^7$ cfu. On the 7th day after the vaccine injection, submandibular blood sampling was carried out and red blood cells was lysed by red blood cell lysis solution, thereby finally obtaining peripheral blood mononuclear cells for ELISPOT assay. The protocol of ELISPOT assay was the same as that in Example 9. Peripheral blood mononuclear cells were stimulated to produce IFN-γ by adding B16-M30 polypeptide into an ELISPOT plate, and finally, the number of spots was quantified by enzyme-linked immunosorbent assay to indicate the specific immune response of each group in response to B16-M30 polypeptide.

Figure 9:
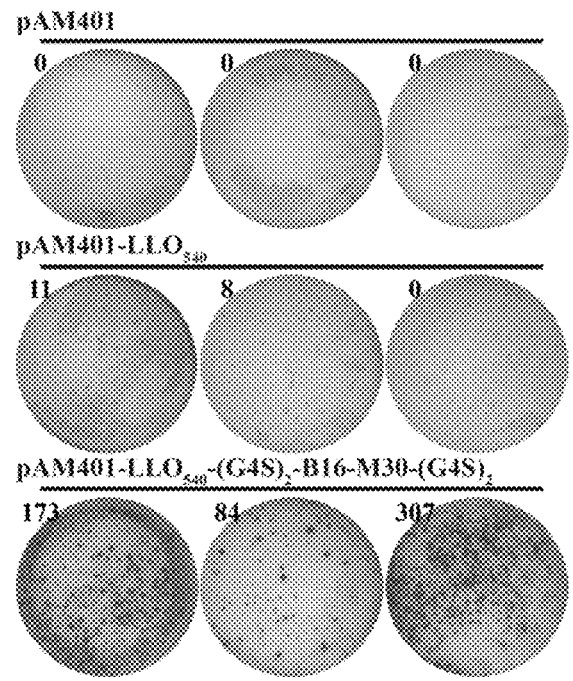
FIG. 9 shows the results of the functional test conducted by means of ELISPOT assay.

The experimental results were as shown in FIG. 9. The results indicated that both pAM401 control group and pAM401-LLO$_{540}$ control group showed no obvious B16-M30-specific immune response while there were many IFN-γ-specific spots generated in pAM401-LLO$_{540}$-(G$_4$S)$_2$-B16-M30-(G$_4$S)$_2$ experimental group, indicating that the intravenous injection of B16-M30 tumor vaccine was capable of stimulating and inducing B16-M30-specific anti-tumor immune response in mice, thereby proving the effectiveness of the non-integrative attenuated *Listeria*-based tumor vaccine constructed by this method.

Example 12: Determination of the Effective Dose of OVA$_{28}$ Tumor Vaccine and the Activation of Tumor-Specific Immune Response in Mice Based on the plasmid obtained in Example 2, the corresponding plasmid adopted in Example 12 was obtained by conventional biological methods in this field. Tumor models were established by subcutaneously inoculating C57 mice (20 mice) with EG7-OVA cells. Taking 10$^7$ cfu as a standard dose, the experiment was carried out by setting multiple gradient doses of OVA$_{28}$ tumor vaccine. The experimental mice were divided into four groups: pAM401-LLO$_{540}$ (10$^7$ cfu) group, pAM401-LLO$_{540}$-(G$_4$S)$_2$-OVA$_{28}$-(G$_4$S)$_2$ (10$^7$ cfu) group, pAM401-LLO$_{540}$-(G$_4$S)$_2$-OVA$_{28}$-(G$_4$S)$_2$ (10$^6$ cfu) group, and pAM401-LLO$_{540}$-(G$_4$S)$_2$-OVA$_{28}$-(G$_4$S)$_2$ (10$^5$ cfu) group. Tumor sizes were measured from the 6th day after the establishment of the EG7-OVA tumor model, the vaccine was injected via tail vein on the 7th day, and the tumor sizes were tracked and measured continuously to obtain the tumor growth curve.

On the 7th day after the vaccine injection, submandibular blood sampling was carried out, and red blood cells was lysed by red blood cell lysis solution, thereby finally obtaining peripheral blood mononuclear cells for ELISPOT assay. The mice were grouped as follows in ELISPOT assay. OT1 mice were set as the positive control group, pAM401-LLO$_{540}$ group was set as experimental control group, and pAM401-LLO$_{540}$-(G$_4$S)$_2$-OVA$_{28}$-(G$_4$S)$_2$ (10$^7$ cfu) group, pAM401-LLO$_{540}$-(G$_4$S)$_2$-OVA$_{28}$-(G$_4$S)$_2$ (10$^6$ cfu) group and pAM401-LLO$_{540}$-(G$_4$S)$_2$-OVA$_{28}$-(G$_4$S)$_2$ (10$^5$ cfu) group were set as experimental groups. Three mice were randomly selected from each group for blood sampling, and peripheral blood mononuclear cells taken from each mice were divided into two aliquots (one aliquot was stimulated with OVA polypeptide, and the other aliquot was not stimulated with OVA polypeptide). The rest protocol of ELISPOT assay was the same as that in Example 9.

Figure 10:
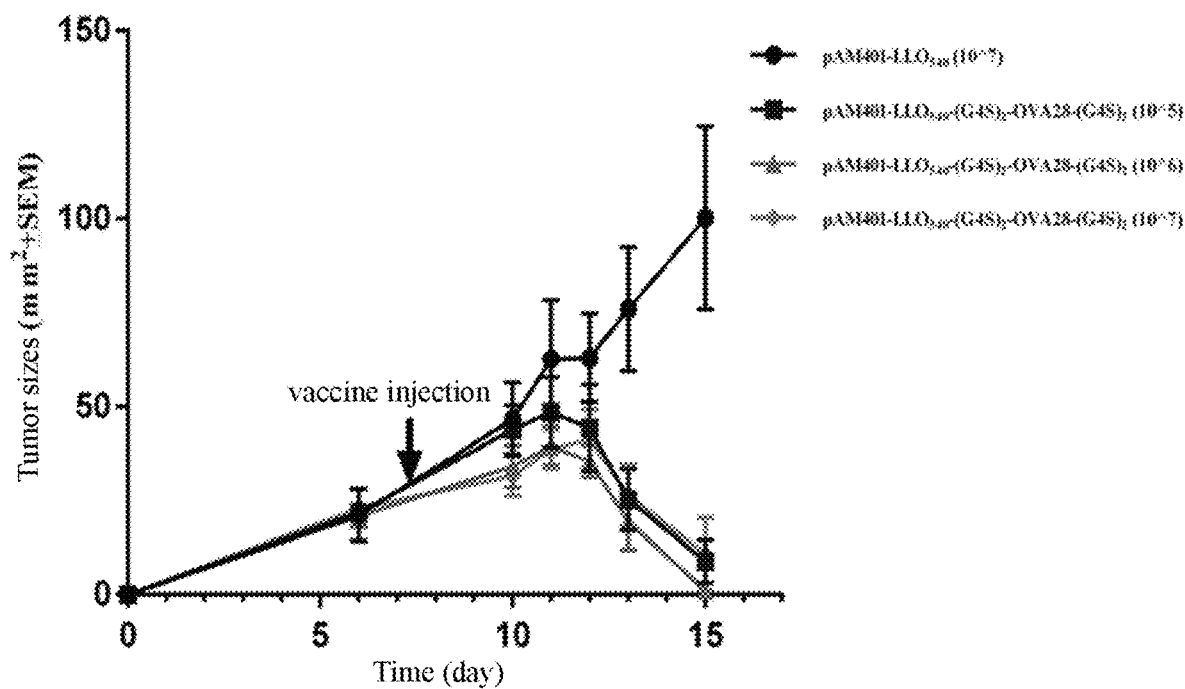
FIG. 10 shows the therapeutic effects on EG7 tumor model after the injection of vaccine of different doses.

The results of the tumor growth curve were as shown in FIG. 10. The results indicated that all the experimental groups (pAM401-LLO$_{540}$-(G$_4$S)$_2$-OVA$_{28}$-(G$_4$S)$_2$ (10$^7$ cfu) group, pAM401-LLO$_{540}$-(G$_4$S)$_2$-OVA$_{28}$-(G$_4$S)$_2$ (10$^6$ cfu) group and pAM401-LLO$_{540}$-(G$_4$S)$_2$-OVA$_{28}$-(G$_4$S)$_2$ (10$^5$ cfu) group) showed a decreasing tendency in tumor size from Day 12 and showed obvious tumor elimination on Day 15. The experiment indicated that OVA$_{28}$ tumor vaccine had obvious tumor-eliminating effect at injection doses of 10$^7$ cfu, 10$^6$ cfu and 10$^5$ cfu.

Figure 11:
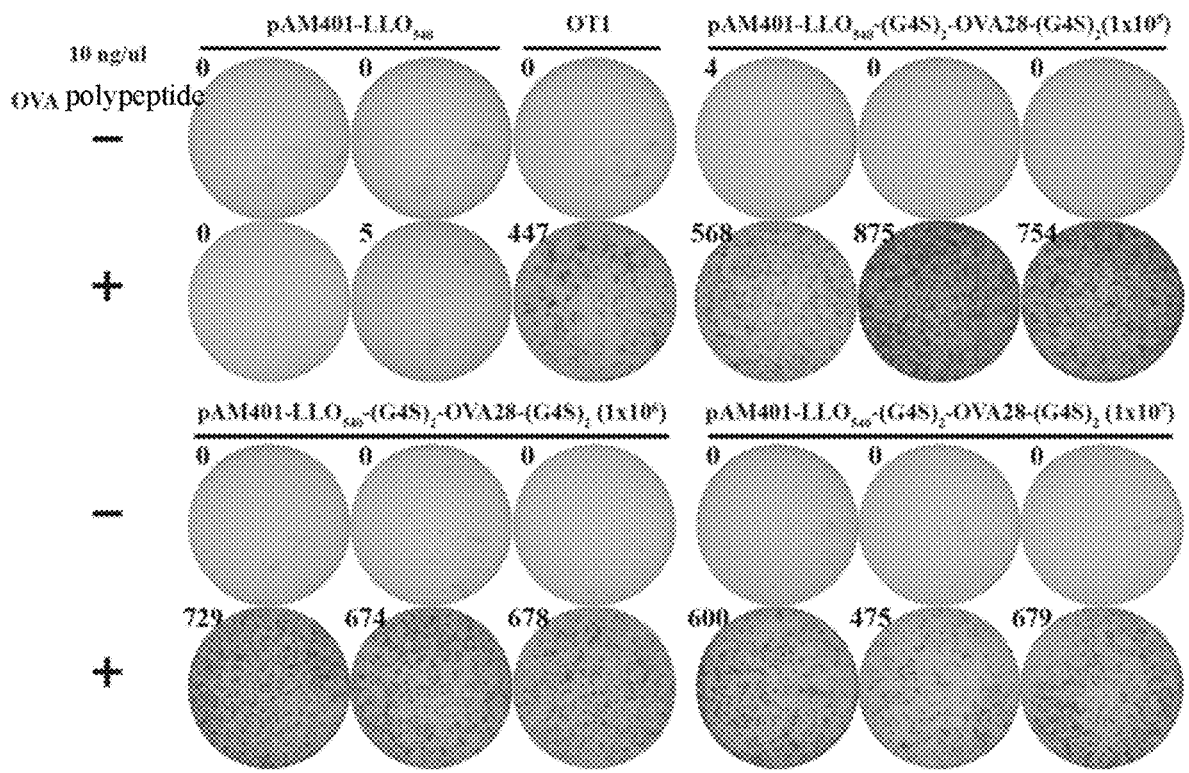
FIG. 11 shows the results of the functional test conducted by means of ELISPOT assay.

The results of ELISPOT assay were as shown in FIG. 11. The results indicated that, among these groups, there was no ELISPOT response in control group in which OVA polypeptide was not added, obvious ELISPOT response appeared in OT1 positive control group in which OVA polypeptide was added for stimulation, and no ELISPOT response appeared in pAM401-LLO$_{540}$ control group in which OVA polypeptide was added for stimulation, thereby suggesting that LLO expressed alone was unable to activate the OVA-specific immune response in the body. However, strong ELISPOT response appeared in all experimental groups (pAM401-LLO$_{540}$-(G$_4$S)$_2$-OVA$_{28}$-(G$_4$S)$_2$ ($10^7$ cfu) group, pAM401-LLO$_{540}$-(G$_4$S)$_2$-OVA$_{28}$-(G$_4$S)$_2$ ($10^6$ cfu) group, and pAM401-LLO$_{540}$-(G$_4$S)$_2$-OVA$_{28}$-(G$_4$S)$_2$ ($10^5$ cfu) group) after the addition of OVA for stimulation. The experiment indicated that OVA$_{28}$ tumor vaccine was capable of activating OVA-specific tumor immune response in mice at injection doses of $10^7$ cfu, $10^6$ cfu and $10^5$ cfu.

Example 13: Determination of the Minimum Effective Dose of OVA$_{28}$ Tumor Vaccine Based on the plasmid obtained in Example 2, the corresponding plasmid adopted in Example 13 was obtained by conventional biological methods in this field. Tumor models were established by subcutaneously inoculating C57 mice (25 mice) with EG7-OVA cells. Taking $10^5$ cfu as a standard dose, this experiment was carried out by setting multiple gradient doses of OVA$_{28}$ tumor vaccine. The experimental mice were divided into five groups: pAM401-LLO$_{540}$ ($10^7$ cfu) group, pAM401-LLO$_{540}$-(G$_4$S)$_2$-OVA$_{28}$-(G$_4$S)$_2$ ($10^5$ cfu) group, pAM401-LLO$_{540}$-(G$_4$S)$_2$-OVA$_{28}$-(G$_4$S)$_2$ ($10^4$ cfu) group, pAM401-LLO$_{540}$-(G$_4$S)$_2$-OVA$_{28}$-(G$_4$S)$_2$ ($10^3$ cfu) group, and pAM401-LLO$_{540}$-(G$_4$S)$_2$-OVA$_{28}$-(G$_4$S)$_2$ ($10^2$ cfu) group. Tumor sizes were measured from the 6th day after the establishment of the EG7-OVA tumor model, the vaccine was injected via tail vein on the 8th day, and the tumor sizes were tracked and measured continuously to obtain the tumor growth curve.

On the 7th day after the vaccine injection, submandibular blood sampling was carried out, and red blood cells was lysed by red blood cell lysis solution, thereby finally obtaining peripheral blood mononuclear cells for ELISPOT assay. The protocol of ELISPOT assay was the same as that in Example 9. Peripheral blood mononuclear cells were stimulated to produce IFN-γ by adding OVA polypeptide into an ELISPOT plate, and finally, the number of spots was quantified by enzyme-linked immunosorbent assay to indicate the specific immune response of each group in response to OVA polypeptide.

Figure 12:
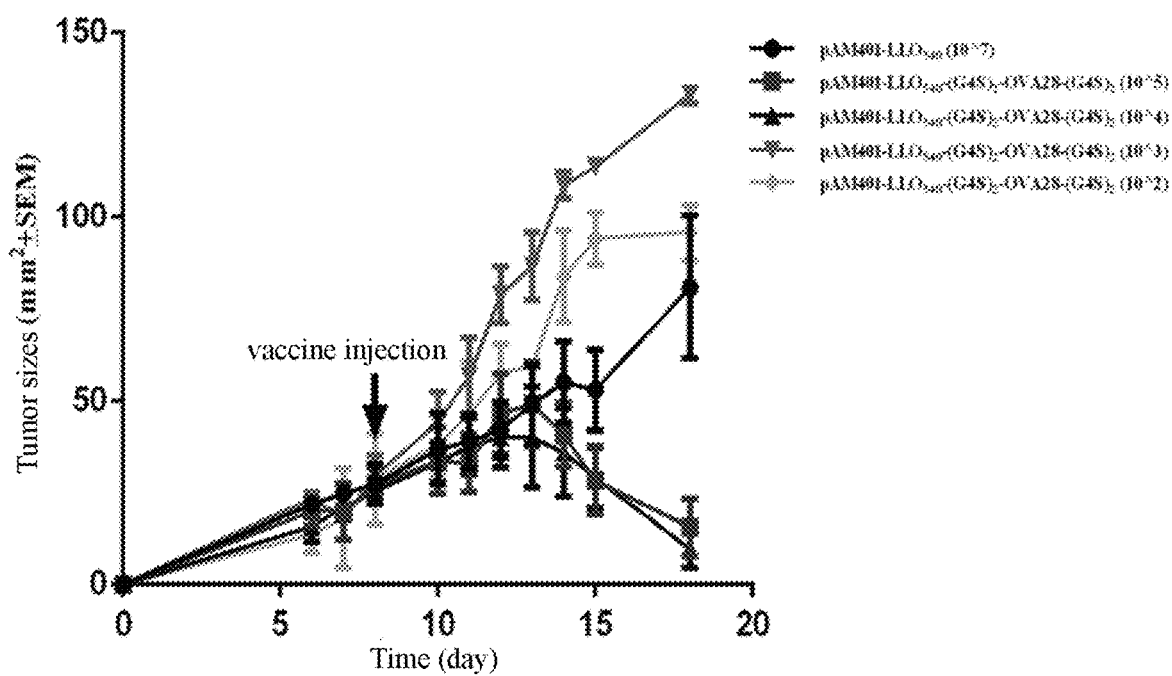
FIG. 12 shows the therapeutic effects on EG7 tumor model after the injection of vaccine of different doses.

The experimental results of the tumor growth curve were as shown in FIG. 12. The results indicated that experimental groups (pAM401-LLO$_{540}$-(G$_4$S)$_2$-OVA$_{28}$-(G$_4$S)$_2$ ($10^5$ cfu) group and pAM401-LLO$_{540}$-(G$_4$S)$_2$-OVA$_{28}$-(G$_4$S)$_2$ ($10^4$ cfu) group) showed a decreasing tendency in tumor size from Day 13 and showed obvious tumor elimination on Day 18. However, in control group (pAM401-LLO$_{540}$ ($10^7$ cfu) group) and experimental groups (pAM401-LLO$_{540}$-(G$_4$S)$_2$-OVA$_{28}$-(G$_4$S)$_2$ ($10^3$ cfu) group and pAM401-LLO$_{540}$-(G$_4$S)$_2$-OVA$_{28}$-(G$_4$S)$_2$ ($10^2$ cfu) group), there was an increasing tendency in tumor size and this tendency lasted up to Day 18. The experiment indicated that the OVA$_{28}$ tumor vaccine still had obvious tumor-eliminating effect at an injection dose of $10^4$ cfu and had no tumor-inhibiting effect when the injection dose was reduced to $10^3$ cfu or $10^2$ cfu. It indicated that the minimum effective dose of the OVA$_{28}$ tumor vaccine constructed by this experimental method was $10^4$ cfu.

Figure 13:
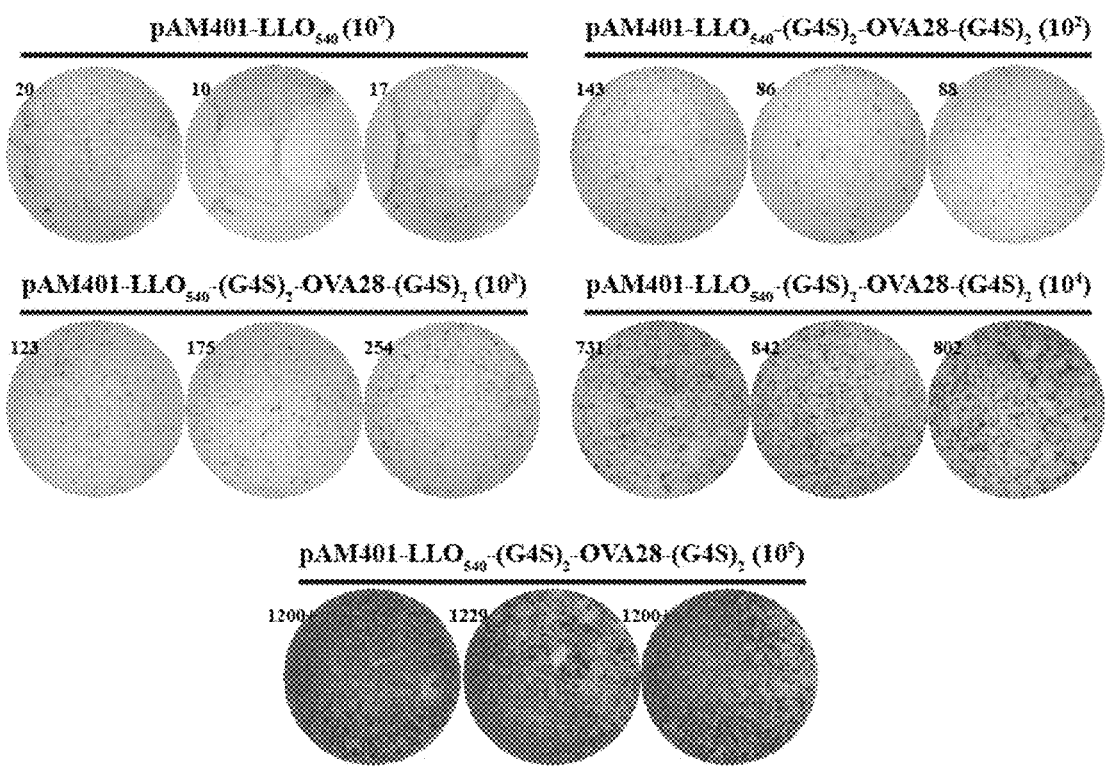
FIG. 13 shows the results of the functional test conducted by means of ELISPOT assay.

The results of ELISPOT assay were as shown in FIG. 13. The results indicated that strong ELISPOT response appeared in experimental groups (pAM401-LLO$_{540}$-(G$_4$S)$_2$-OVA$_{28}$-(G$_4$S)$_2$ ($10^5$ cfu) group and pAM401-LLO$_{540}$-(G$_4$S)$_2$-OVA$_{28}$-(G$_4$S)$_2$ ($10^4$ cfu) group) while the ELISPOT responses in experimental groups (pAM401-LLO$_{540}$-(G$_4$S)$_2$-OVA$_{28}$-(G$_4$S)$_2$ ($10^3$ cfu) group and pAM401-LLO$_{540}$-(G$_4$S)$_2$-OVA$_{28}$-(G$_4$S)$_2$ ($10^2$ cfu) group) were relatively weak. The experiment indicated that the OVA$_{28}$ tumor vaccine was also capable of significantly activating OVA-specific tumor immune response in mice at an injection dose of $10^4$ cfu.

Example 14: Efficacy Comparison Between OVA$_{28}$ Tumor Vaccine and OVA-Integrated *Listeria*-Based Vaccine Based on the plasmid obtained in Example 2, the corresponding plasmid adopted in Example 14 was obtained by conventional biological methods in this field. Tumor models were established by subcutaneously inoculating C57 mice (20 mice) with EG7-OVA cells. The experimental mice were divided into four groups: LM ΔactA (pAM401) as control group (non-integrative), LM ΔactA (pAM401-LLO$_{540}$-(G$_4$S)$_2$-OVA$_{28}$-(G$_4$S)$_2$) as experimental group (non-integrative); LM ΔactA as control group (integrative), and LM-OVA ΔactA as experimental group (integrative). Tumor sizes were measured from the 6th day after the establishment of the EG7-OVA tumor model, the vaccine was injected via tail vein on the 7th day (the injection dose was $10^5$ cfu), and the tumor sizes were tracked and measured continuously to obtain the tumor growth curve.

Similarly, ELISPOT assay was used to conduct functional verification. On the 7th day after the vaccine injection, submandibular blood sampling was carried out, and red blood cells was lysed by red blood cell lysis solution, thereby finally obtaining peripheral blood mononuclear cells for ELISPOT assay. The protocol of ELISPOT assay was the same as that in Example 9. Peripheral blood mononuclear cells were stimulated to produce IFN-γ by adding OVA polypeptide into an ELISPOT plate, and finally, the number of spots was quantified by enzyme-linked immunosorbent assay to indicate the specific immune response of each group in response to OVA polypeptide. Next, on Day 12, the blood was collected by removing eyeballs and the spleen tissue was incised for ELISPOT assay. The amount of the peripheral blood mononuclear cells inoculated was $1 \times 10^5$ cells to $10 \times 10^5$ cells, which was the same as that in the previous experiment. The spleen tissue was grinded, allowed to pass a 75-μm filter and the cells were collected by centrifugation, and the inoculation amount was $1 \times 10^5$ cells and $1 \times 10^6$ cells in the experiment.

Figure 14:
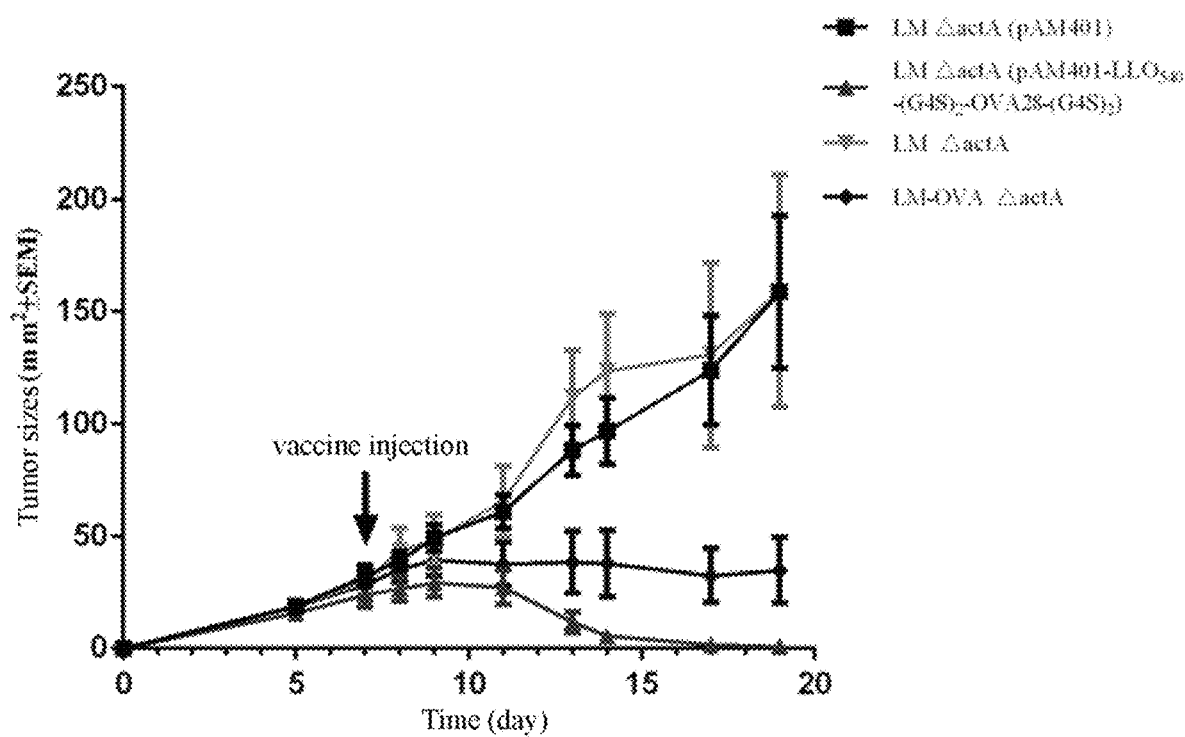
FIG. 14 shows the comparison of the efficacy on tumor between the tumor vaccine of the present disclosure and the OVA-integrated *Listeria*.

The experimental results of the tumor growth curve were as shown in FIG. 14. The tumor sizes in LM ΔactA (pAM401) group (control group) and LM ΔactA group (control group) were in a state of continuous growth. In LM ΔactA (pAM401-LLO$_{540}$-(G$_4$S)$_2$-OVA$_{28}$-(G$_4$S)$_2$) group (experimental group), the reduction of tumor sizes started from Day 11 and the tumors were significantly eliminated on Day 17. In LM-OVA ΔactA group (experimental group), the tumor sizes were controlled until the 19th day after the injection of the vaccine and there was neither obvious growth nor obvious elimination. The experimental results indicated that the OVA$_{28}$ tumor vaccine (non-integrative) constructed by this experimental method had better tumor-eliminating effect as compared with the OVA-integrated *Listeria*-based vaccine.

Figure 15:
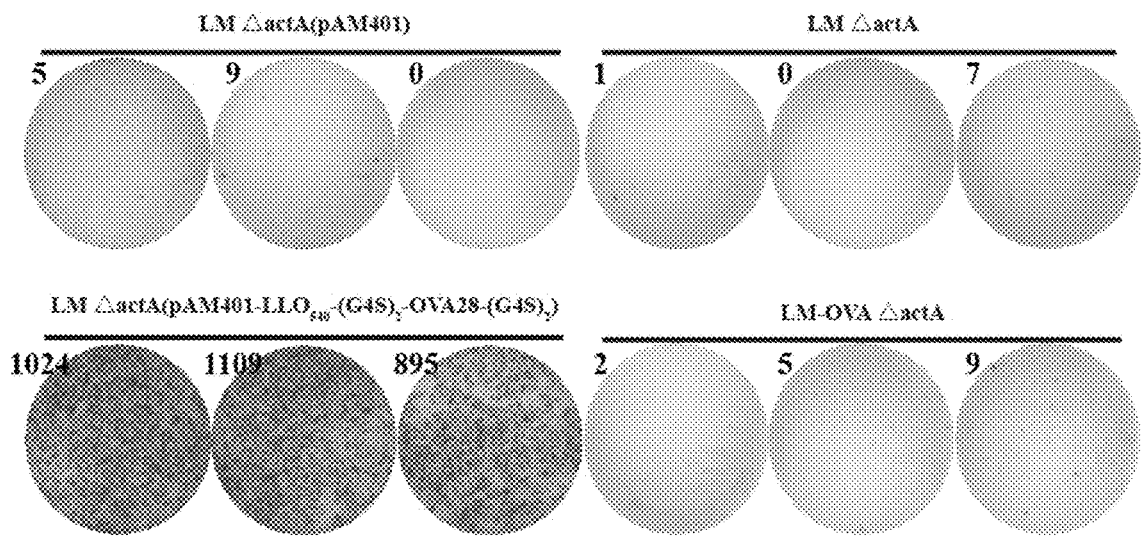
FIG. 15 shows the results of the functional test conducted by means of ELISPOT assay 7 days after vaccine injection.

The results of the ELISPOT assay conducted 7 days later were as shown in FIG. 15. There was no obvious ELISPOT response in LM ΔactA (pAM401) group and LM ΔactA group (control groups) and LM-OVA ΔactA group (experimental group), while there was obvious and strong ELISPOT response in LM ΔactA (pAM401-LLO$_{540}$-(G$_4$S)$_2$-OVA$_{28}$-(G$_4$S)$_2$) group (experimental group). It indicated that the OVA$_{28}$ tumor vaccine (non-integrative) constructed by this experimental method was capable of better activating tumor-specific immune response in vivo as compared with the OVA-integrated *Listeria*-based vaccine.

Figure 16:
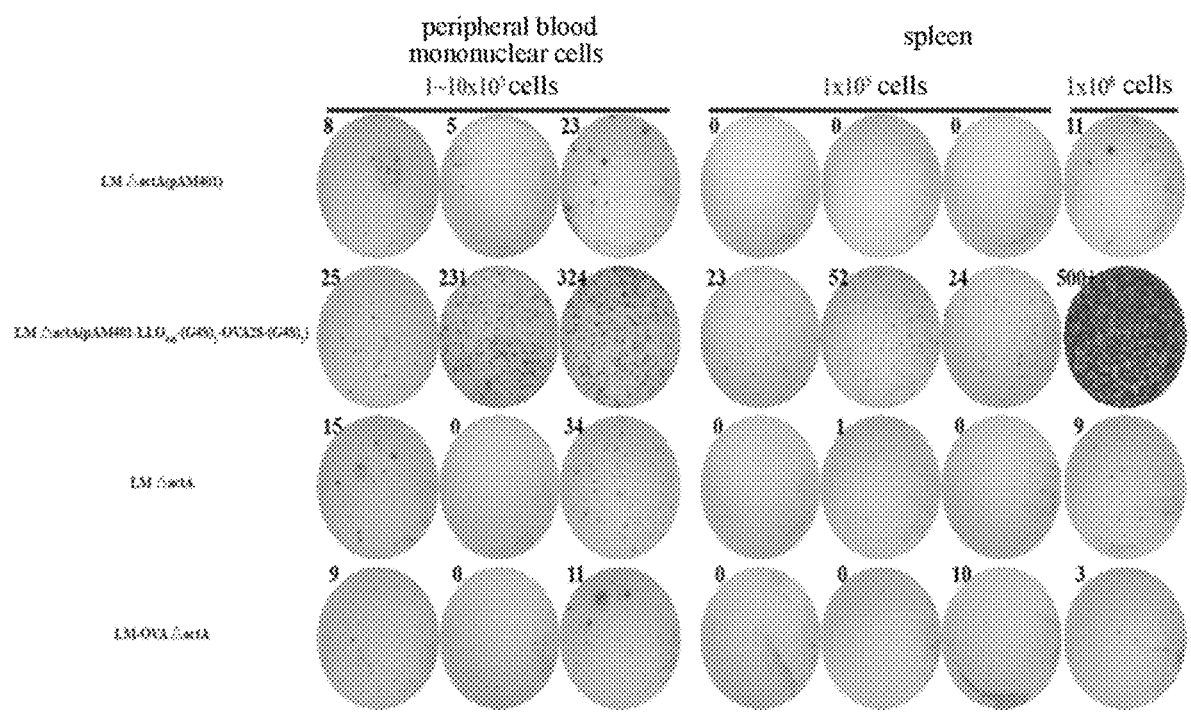
FIG. 16 shows the results of the functional test conducted by means of ELISPOT assay 12 days after vaccine injection.

The results of the ELISPOT assay conducted 12 days later were as shown in FIG. 16. Consistent with the results of the ELISPOT assay on Day 7, there was no obvious ELISPOT response in LM-OVA ΔactA group (experimental group), while there were obvious and strong ELISPOT responses in both peripheral blood mononuclear cells and spleen tissue of LM ΔactA (pAM401-LLO$_{540}$-(G$_4$S)$_2$-OVA$_{28}$-(G$_4$S)$_2$) group (experimental group).

Example 15: OVA$_{28}$ Tumor Vaccine is not OVA-Integrated *Listeria*-Based Vaccine An LM strain obtained from the aforementioned Examples of the present disclosure was taken. For example, in one embodiment, LM 10403 SΔactA (pAM401-hly-LLO$_{540}$-(G$_4$S)$_2$-OVA$_{28}$-(G$_4$S)$_2$-His) strain was taken. After the microbes were shaken overnight, the plasmid was extracted and electrotransformed into new Competent LM which were then spread on a CM-resistant plate, and the Competent LM that were not subjected to electrotransformation were spread on the plate as negative control. For the electrotransformation method, please refer to the corresponding protocol in Example 3 of the present disclosure.

Figure 17:
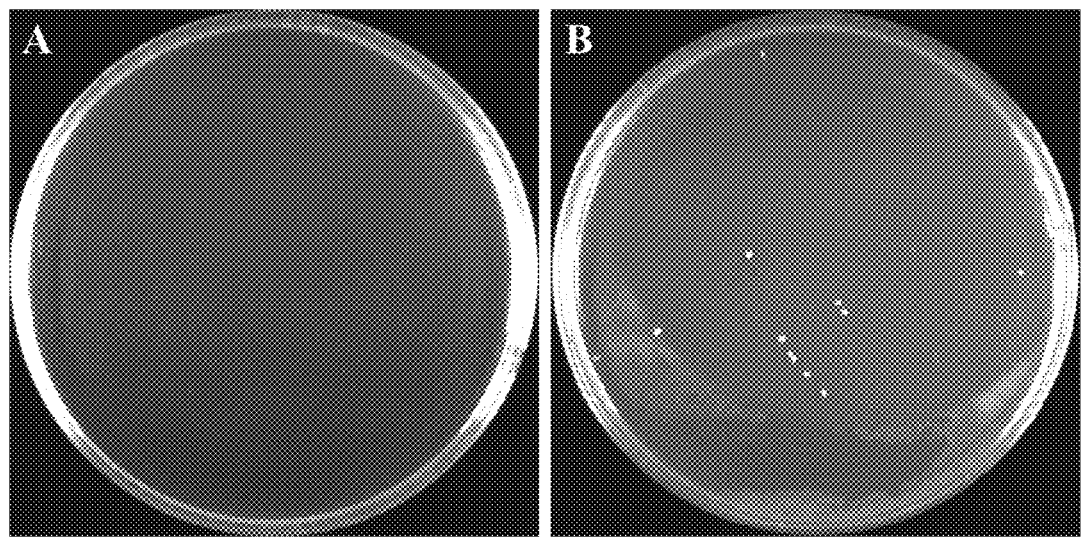
FIG. 17 shows the culture results of the strain which is spread on a CM-resistant plate after the plasmid pAM401-hly-LLO$_{540}$-(G$_4$S)$_2$-OVA$_{28}$-(G$_4$S)$_2$-His has been electrotransformed thereto, wherein FIG. A shows the CM-resistant plate spread with competent LM wherein the plasmid pAM401-hly-LLO$_{540}$-(G$_4$S)$_2$-OVA$_{28}$-(G$_4$S)$_2$-His have not been electrotransformed thereto, and FIG. B shows the CM-resistant plate spread with Competent LM wherein the plasmid pAM401-hly-LLO$_{540}$-(G$_4$S)$_2$-OVA$_{28}$-(G$_4$S)$_2$-His have been electrotransformed thereto.

By the method of electrotransforming the plasmid into Competent LM, only LM electrotransformed with the plasmid could survive under CM resistance. The results of the aforementioned inoculated plates were as shown in FIG. 17.

As for the LM colonies obtained after plating, the full-length DNA of the strain in the above-mentioned colonies was extracted by conventional biological methods in this field. LM 10403 SΔactA strain was used as a negative control, and the plasmid pAM401-hly-LLO$_{540}$-(G$_4$S)$_2$-OVA$_{28}$-(G$_4$S)$_2$-His was used as a positive control. Agarose gel electrophoresis (1%) was conducted, and then the genomic DNA and plasmid DNA of LM on the gel were extracted by gel cutting so as to obtain the purified genomic DNA and plasmid DNA of LM. Afterwards, the sequence of OVA$_{28}$ was amplified by PCR reaction using each purified DNA obtained above as a template, and then identified by agarose gel electrophoresis.

Figure 18:
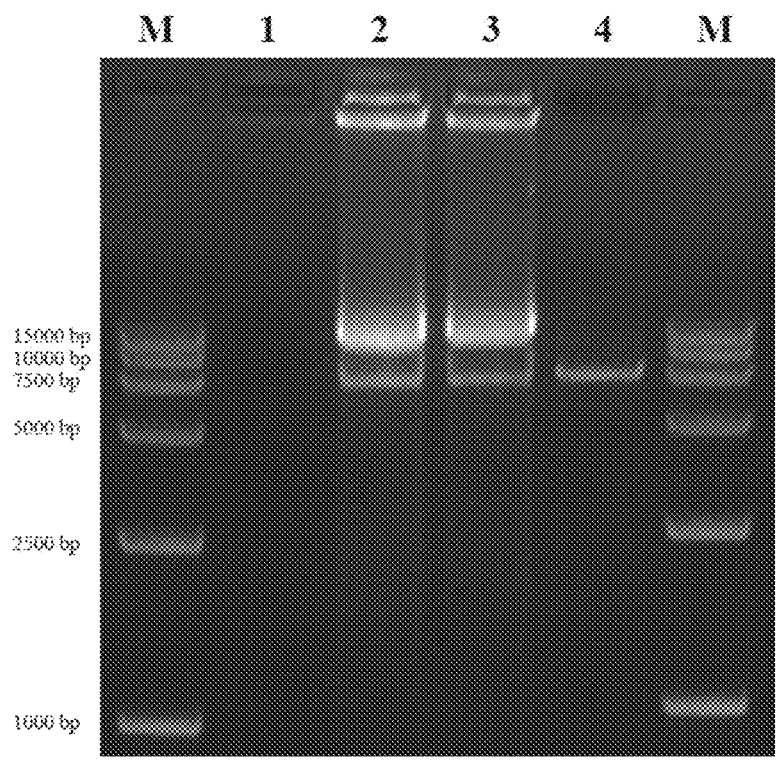
FIG. 18 shows the PCR results of the purified genomic DNA and plasmid DNA of the strain comprising the plasmid pAM401-hly-LLO$_{540}$-(G$_4$S)$_2$-OVA$_{28}$-(G$_4$S)$_2$-His, wherein Lane M shows 15000-bp DNA ladder as standard reference, Lane 1 shows the genomic DNA of LM 10403SΔactA strain, Lanes 2 and 3 respectively show the full-length DNA of LM 10403 SΔactA (pAM401-hly-LLO$_{540}$-(G$_4$S)$_2$-OVA$_{28}$-(G$_4$S)$_2$-His) strain, and Lane 4 shows the DNA of the plasmid pAM401-hly-LLO$_{540}$-(G$_4$S)$_2$-OVA$_{28}$-(G$_4$S)$_2$-His.
Figure 19:
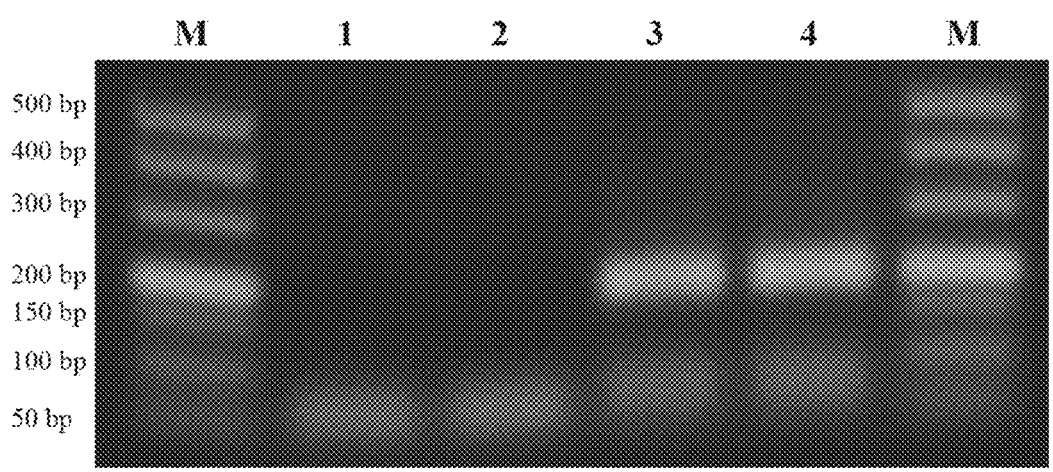
FIG. 19 shows the PCR results of the purified genomic DNA and plasmid DNA of the strain comprising the plasmid pAM401-hly-LLO$_{540}$-(G$_4$S)$_2$-OVA$_{28}$-(G$_4$S)$_2$-His, wherein Lane M shows 500-bp DNA ladder as standard reference, Lanes 1 and 2 show the PCR product using the genomic DNA of LM 10403 SΔactA (pAM401-hly-LLO$_{540}$-(G$_4$S)$_2$-

The identification results of agarose gel electrophoresis were as shown in FIGS. 18 and 19. It was confirmed by molecular experiments that using the genomic DNA of LM 10403SΔactA (pAM401-hly-LLO$_{540}$-(G$_4$S)$_2$-OVA$_{28}$-(G$_4$S)$_2$-His) strain as a template for PCR did not produce the target gene sequence while using the plasmid DNA of LM 10403 SΔactA (pAM401-hly-LLO$_{540}$-(G$_4$S)$_2$-OVA$_{28}$-(G$_4$S)$_2$-His) strain as a template for PCR produced the target gene band with correct size (the size of the target band was 200 bp, and primer dimer was located at 50 bp). The above-mentioned experimental results indicated that the target gene only existed on the plasmid and would not be integrated into the genomic DNA. As a result, it was proved that the LM vaccine constructed by using the method of the present disclosure was a non-integrative LM vaccine.

The above-mentioned Examples of the present disclosure are merely exemplified to clearly illustrate the present disclosure rather than limitations to the embodiments of the present disclosure. For those of ordinary skill in the art, other changes or modifications in different forms may also be made based on the foregoing description. It is not necessary and impossible to enumerate all the embodiments. Any modification, equivalent replacement and improvement made within the spirits and principles of this disclosure shall be encompassed in the protection scope of the claims of the present disclosure.

What is claimed is:

1. A recombinant nucleic acid molecule comprising an open reading frame encoding a recombinant polypeptide, wherein the recombinant polypeptide comprises a heterologous antigen fused to a derived Listeriolysin O (LLO) polypeptide, wherein the recombinant nucleic acid molecule further comprises a first promoter sequence, wherein the derived Listeriolysin O (LLO) polypeptide comprises
an amino acid sequence as set forth in SEQ ID NO:4, and wherein the LLO polypeptide has or partially has the activity of an Listeriolysin O (LLO) polypeptide as set forth in SEQ ID NO:2.

2. The recombinant nucleic acid molecule of claim 1, wherein the derived Listeriolysin O (LLO) polypeptide consists of a polypeptide as set forth in SEQ ID NO: 4.

3. The recombinant nucleic acid molecule of claim 1, wherein the heterologous antigen is selected from tumor antigens or non-tumor antigens, wherein the non-tumor antigens are selected from ovalbumin (OVA) or fragments having the function of OVA.

4. The recombinant nucleic acid molecule of claim 3, wherein an amino acid sequence of said OVA or an amino acid fragment having the function of OVA is selected from amino acid sequences comprising an amino acid sequence as set forth in SEQ ID NO:9 or SEQ ID NO:10.

5. The recombinant nucleic acid molecule of claim 1, further comprising a linking sequence that links a nucleotide sequence encoding the derived Listeriolysin O (LLO) polypeptide and a nucleotide sequence encoding the heterologous antigen,
wherein the heterologous antigen is selected from tumor antigens or non-tumor antigens wherein the non-tumor antigens are selected from OVA or fragments having the function of OVA.

6. The recombinant nucleic acid molecule of claim 5, wherein an amino acid sequence, encoded by a nucleotide sequence which is connected to the nucleotide sequence of the derived Listeriolysin O (LLO) polypeptide and comprises a linking sequence and the nucleotide sequence of the heterologous antigen, is as set forth in SEQ ID NO:15 or SEQ ID NO:16.

7. The recombinant nucleic acid molecule of claim 1, wherein the promoter sequence is the sequence encoded by Phly gene, wherein the recombinant nucleic acid molecule further comprises a tag sequence for detection or a gene encoding a metabolite.

8. A recombinant plasmid or a recombinant expression vector, comprising the sequence of the recombinant nucleic acid molecule of claim 1.

9. The recombinant nucleic acid molecule of claim 1, wherein the open reading frame encoding the recombinant polypeptide comprises a gene encoding the heterologous antigen inserted downstream of the sequence encoding amino acid 1-28 of SEQ ID NO: 4 and the sequence encoding amino acids 29-540 of SEQ ID NO: 4.

10. The recombinant nucleic acid molecule of claim 1, wherein the open reading frame encoding the recombinant polypeptide comprises a gene encoding the heterologous antigen inserted between the sequence encoding amino acids 1-523 of SEQ ID NO: 4 and the sequence encoding amino acids 524-540 of SEQ ID NO: 4.

11. A recombinant *Listeria* comprising the recombinant nucleic acid molecule of claim 1.

12. A pharmaceutical composition comprising a therapeutically effective amount of the recombinant *Listeria* of claim 11.

13. A prophylactic or therapeutic vaccine, wherein the vaccine comprises a prophylactically or therapeutically effective amount of the recombinant *Listeria* of claim 11.

14. A recombinant nucleic acid molecule comprising an open reading frame encoding an amino acid sequence as set forth in SEQ ID NO: 4.

15. The recombinant nucleic acid molecule of claim 14, comprising a sequence as set forth in SEQ ID NO: 3.

* * * * *

SEQUENCE LISTING

<160> NUMBER OF SEQ ID NOS: 16

<210> SEQ ID NO 1
<211> LENGTH: 1587
<212> TYPE: DNA
<213> ORGANISM: Listeria monocytogenes

<400> SEQUENCE: 1

```
atgaaaaaaa taatgctagt ttttattaca cttatattag ttagtctacc aattgcgcaa      60
caaactgaag caaaggatgc atctgcattc aataaagaaa attcaatttc atccatggca     120
ccaccagcat ctccgcctgc aagtcctaag acgccaatcg aaaagaaaca cgcggatgaa     180
atcgataagt atatacaagg attggattac aataaaaaca atgtattagt ataccacgga     240
gatgcagtga caaatgtgcc gccaagaaaa ggttacaaag atggaaatga atatattgtt     300
gtggagaaaa agaagaaatc catcaatcaa aataatgcag acattcaagt tgtgaatgca     360
atttcgagcc taacctatcc aggtgctctc gtaaaagcga attcggaatt agtagaaaat     420
caaccagatg ttctccctgt aaaacgtgat tcattaacac tcagcattga tttgccaggt     480
atgactaatc aagacaataa aatagttgta aaaaatgcca ctaaatcaaa cgttaacaac     540
gcagtaaata cattagtgga aagatggaat gaaaatatg ctcaagctta tccaaatgta     600
agtgcaaaaa ttgattatga tgacgaaatg gcttacagtg aatcacaatt aattgcgaaa     660
tttggtacag catttaaagc tgtaaataat agcttgaatg taaacttcgg cgcaatcagt     720
gaagggaaaa tgcaagaaga agtcattagt tttaaacaaa tttactataa cgtgaatgtt     780
```

```
aatgaaccta caagaccttc cagattttc ggcaaagctg ttactaaaga gcagttgcaa    840
gcgcttggag tgaatgcaga aaatcctcct gcatatatct caagtgtggc gtatggccgt    900
caagtttatt tgaaattatc aactaattcc catagtacta agtaaaagc tgcttttgat    960
gctgccgtaa gcggaaaatc tgtctcaggt gatgtagaac taacaaatat catcaaaaat   1020
tcttccttca agccgtaat ttacggaggt tccgcaaaag atgaagttca atcatcgac    1080
ggcaacctcg gagacttacg cgatattttg aaaaaaggcg ctacttttaa tcgagaaaca   1140
ccaggagttc ccattgctta taacaaac ttcctaaaag acaatgaatt agctgttatt    1200
aaaaacaact cagaatatat tgaaacaact tcaaaagctt atacagatgg aaaaattaac   1260
atcgatcact ctggaggata cgttgctcaa ttcaacattt cttgggatga agtaaattat   1320
gatcctgaag gtaacgaaat tgttcaacat aaaaactgga gcgaaaacaa taaaagcaag   1380
ctagctcatt tcacatcgtc catctatttg cctggtaacg cgagaaatat taatgtttac   1440
gctaaagaat gcactggttt agcttgggaa tggtggagaa cggtaattga tgaccggaac   1500
ttaccacttg tgaaaaatag aaatatctcc atctggggca ccacgcttta tccgaaatat   1560
agtaataaag tagataatcc aatcgaa                                      1587

<210> SEQ ID NO 2
<211> LENGTH: 529
<212> TYPE: PRT
<213> ORGANISM: Listeria monocytogenes

<400> SEQUENCE: 2

Met Lys Lys Ile Met Leu Val Phe Ile Thr Leu Ile Leu Val Ser Leu
1               5                   10                  15

Pro Ile Ala Gln Gln Thr Glu Ala Lys Asp Ala Ser Ala Phe Asn Lys
            20                  25                  30

Glu Asn Ser Ile Ser Ser Met Ala Pro Pro Ala Ser Pro Pro Ala Ser
        35                  40                  45

Pro Lys Thr Pro Ile Glu Lys Lys His Ala Asp Glu Ile Asp Lys Tyr
    50                  55                  60

Ile Gln Gly Leu Asp Tyr Asn Lys Asn Asn Val Leu Val Tyr His Gly
65                  70                  75                  80

Asp Ala Val Thr Asn Val Pro Pro Arg Lys Gly Tyr Lys Asp Gly Asn
                85                  90                  95

Glu Tyr Ile Val Val Glu Lys Lys Lys Ser Ile Asn Gln Asn Asn
            100                 105                 110

Ala Asp Ile Gln Val Val Asn Ala Ile Ser Ser Leu Thr Tyr Pro Gly
        115                 120                 125

Ala Leu Val Lys Ala Asn Ser Glu Leu Val Glu Asn Gln Pro Asp Val
    130                 135                 140

Leu Pro Val Lys Arg Asp Ser Leu Thr Leu Ser Ile Asp Leu Pro Gly
145                 150                 155                 160

Met Thr Asn Gln Asp Asn Lys Ile Val Val Lys Asn Ala Thr Lys Ser
                165                 170                 175

Asn Val Asn Ala Val Asn Thr Leu Val Glu Arg Trp Asn Glu Lys
            180                 185                 190

Tyr Ala Gln Ala Tyr Pro Asn Val Ser Ala Lys Ile Asp Tyr Asp Asp
        195                 200                 205

Glu Met Ala Tyr Ser Glu Ser Gln Leu Ile Ala Lys Phe Gly Thr Ala
    210                 215                 220
```

Phe Lys Ala Val Asn Asn Ser Leu Asn Val Asn Phe Gly Ala Ile Ser
225                 230                 235                 240

Glu Gly Lys Met Gln Glu Val Ile Ser Phe Lys Gln Ile Tyr Tyr
            245                 250                 255

Asn Val Asn Val Asn Glu Pro Thr Arg Pro Ser Arg Phe Phe Gly Lys
            260                 265                 270

Ala Val Thr Lys Glu Gln Leu Gln Ala Leu Gly Val Asn Ala Glu Asn
            275                 280                 285

Pro Pro Ala Tyr Ile Ser Ser Val Ala Tyr Gly Arg Gln Val Tyr Leu
            290                 295                 300

Lys Leu Ser Thr Asn Ser His Ser Thr Lys Val Lys Ala Ala Phe Asp
305                 310                 315                 320

Ala Ala Val Ser Gly Lys Ser Val Ser Gly Asp Val Glu Leu Thr Asn
                325                 330                 335

Ile Ile Lys Asn Ser Ser Phe Lys Ala Val Ile Tyr Gly Gly Ser Ala
                340                 345                 350

Lys Asp Glu Val Gln Ile Ile Asp Gly Asn Leu Gly Asp Leu Arg Asp
            355                 360                 365

Ile Leu Lys Lys Gly Ala Thr Phe Asn Arg Glu Thr Pro Gly Val Pro
370                 375                 380

Ile Ala Tyr Thr Thr Asn Phe Leu Lys Asp Asn Glu Leu Ala Val Ile
385                 390                 395                 400

Lys Asn Asn Ser Glu Tyr Ile Glu Thr Thr Ser Lys Ala Tyr Thr Asp
                405                 410                 415

Gly Lys Ile Asn Ile Asp His Ser Gly Gly Tyr Val Ala Gln Phe Asn
            420                 425                 430

Ile Ser Trp Asp Glu Val Asn Tyr Asp Pro Glu Gly Asn Glu Ile Val
            435                 440                 445

Gln His Lys Asn Trp Ser Glu Asn Asn Lys Ser Lys Leu Ala His Phe
450                 455                 460

Thr Ser Ser Ile Tyr Leu Pro Gly Asn Ala Arg Asn Ile Asn Val Tyr
465                 470                 475                 480

Ala Lys Glu Cys Thr Gly Leu Ala Trp Glu Trp Trp Arg Thr Val Ile
                485                 490                 495

Asp Asp Arg Asn Leu Pro Leu Val Lys Asn Arg Asn Ile Ser Ile Trp
            500                 505                 510

Gly Thr Thr Leu Tyr Pro Lys Tyr Ser Asn Lys Val Asp Asn Pro Ile
            515                 520                 525

Glu

<210> SEQ ID NO 3
<211> LENGTH: 1620
<212> TYPE: DNA
<213> ORGANISM: Listeria monocytogenes

<400> SEQUENCE: 3
atgaaaaaaa taatgctagt tttttattaca cttatattag ttagtctacc aattgcgcaa      60
caaactgaag caaggatgc atcggatcct actgaagcaa aggatgcatc tgcattcaat      120
aaagaaaatt caatttcatc catggcacca ccagcatctc cgcctgcaag tcctaagacg      180
ccaatcgaaa agaaacacgc ggatgaaatc gataagtata caaggatt ggattacaat      240 aaaaacaatg tattagtata ccacggagat gcagtgacaa atgtgccgcc aagaaaaggt      300
tacaaagatg gaaatgaata tattgttgtg gagaaaaaga gaaatccat caatcaaaat      360

```
aatgcagaca ttcaagttgt gaatgcaatt tcgagcctaa cctatccagg tgctctcgta    420
aaagcgaatt cggaattagt agaaaatcaa ccagatgttc tccctgtaaa acgtgattca    480
ttaacactca gcattgattt gccaggtatg actaatcaag acaataaaat cgttgtaaaa    540
aatgccacta aatcaaacgt taacaacgca gtaaatacat tagtggaaag atggaatgaa    600
aaatatgctc aagcttatcc aaatgtaagt gcaaaattg attatgatga cgaaatggct    660
tacagtgaat cacaattaat tgcgaaattt ggtacagcat ttaaagctgt aaataatagc    720
ttgaatgtaa acttcggcgc aatcagtgaa gggaaaatgc aagaagaagt cattagtttt    780
aaacaaattt actataacgt gaatgttaat gaacctacaa gaccttccag atttttcggc    840
aaagctgtta ctaaagagca gttgcaagcg cttggagtga atgcagaaaa tcctcctgca    900
tatatctcaa gtgtggcgta tggccgtcaa gtttatttga aattatcaac taattcccat    960
agtactaaag taaagctgc ttttgatgct gccgtaagcg aaaatctgt ctcaggtgat    1020 gtagaactaa caaatatcat caaaaattct tccttcaaag ccgtaattta cggaggttcc    1080
gcaaaagatg aagttcaaat catcgacggc aacctcggag acttacgcga tattttgaaa    1140
aaaggcgcta cttttaatcg agaaacacca ggagttccca ttgcttatac aacaaacttc    1200
ctaaaagaca atgaattagc tgttattaaa aacaactcag aatatattga aacaacttca    1260
aaagcttata cagatggaaa aattaacatc gatcactctg gaggatacgt tgctcaattc    1320
aacatttctt gggatgaagt aaattatgat cctgaaggta acgaaattgt tcaacataaa    1380
aactggagcg aaaacaataa aagcaagcta gctcatttca catcgtccat ctatttgcca    1440
ggtaacgcga aaatattaa tgtttacgct aaagaatgca ctggtttagc ttgggaatgg    1500
tggagaacgg taattgatga ccggaactta ccacttgtga aaaatagaaa tatctccatc    1560
tggggcacca cgctttatcc gaaatatagt aataaactgc aggtagataa tccaatcgaa    1620
```

<210> SEQ ID NO 4
<211> LENGTH: 540
<212> TYPE: PRT
<213> ORGANISM: Listeria monocytogenes

<400> SEQUENCE: 4

```
Met Lys Lys Ile Met Leu Val Phe Ile Thr Leu Ile Leu Val Ser Leu
1               5                   10                  15

Pro Ile Ala Gln Gln Thr Glu Ala Lys Asp Ala Ser Asp Pro Thr Glu
            20                  25                  30

Ala Lys Asp Ala Ser Ala Phe Asn Lys Glu Asn Ser Ile Ser Ser Met
        35                  40                  45

Ala Pro Pro Ala Ser Pro Pro Ala Ser Pro Lys Thr Pro Ile Glu Lys
    50                  55                  60

Lys His Ala Asp Glu Ile Asp Lys Tyr Ile Gln Gly Leu Asp Tyr Asn
65                  70                  75                  80

Lys Asn Asn Val Leu Val Tyr His Gly Asp Ala Val Thr Asn Val Pro
                85                  90                  95

Pro Arg Lys Gly Tyr Lys Asp Gly Asn Glu Tyr Ile Val Val Glu Lys
            100                 105                 110

Lys Lys Lys Ser Ile Asn Gln Asn Asn Ala Asp Ile Gln Val Val Asn
        115                 120                 125

Ala Ile Ser Ser Leu Thr Tyr Pro Gly Ala Leu Val Lys Ala Asn Ser
    130                 135                 140
```

```
Glu Leu Val Glu Asn Gln Pro Asp Val Leu Pro Val Lys Arg Asp Ser
145                 150                 155                 160

Leu Thr Leu Ser Ile Asp Leu Pro Gly Met Thr Asn Gln Asp Asn Lys
                165                 170                 175

Ile Val Val Lys Asn Ala Thr Lys Ser Asn Val Asn Asn Ala Val Asn
            180                 185                 190

Thr Leu Val Glu Arg Trp Asn Glu Lys Tyr Ala Gln Ala Tyr Pro Asn
        195                 200                 205

Val Ser Ala Lys Ile Asp Tyr Asp Glu Met Ala Tyr Ser Glu Ser
    210                 215                 220

Gln Leu Ile Ala Lys Phe Gly Thr Ala Phe Lys Ala Val Asn Asn Ser
225                 230                 235                 240

Leu Asn Val Asn Phe Gly Ala Ile Ser Glu Gly Lys Met Gln Glu Glu
                245                 250                 255

Val Ile Ser Phe Lys Gln Ile Tyr Tyr Asn Val Asn Val Asn Glu Pro
            260                 265                 270

Thr Arg Pro Ser Arg Phe Phe Gly Lys Ala Val Thr Lys Glu Gln Leu
        275                 280                 285

Gln Ala Leu Gly Val Asn Ala Glu Asn Pro Pro Ala Tyr Ile Ser Ser
290                 295                 300

Val Ala Tyr Gly Arg Gln Val Tyr Leu Lys Leu Ser Thr Asn Ser His
305                 310                 315                 320

Ser Thr Lys Val Lys Ala Ala Phe Asp Ala Ala Val Ser Gly Lys Ser
                325                 330                 335

Val Ser Gly Asp Val Glu Leu Thr Asn Ile Ile Lys Asn Ser Ser Phe
            340                 345                 350

Lys Ala Val Ile Tyr Gly Gly Ser Ala Lys Asp Glu Val Gln Ile Ile
        355                 360                 365

Asp Gly Asn Leu Gly Asp Leu Arg Asp Ile Leu Lys Lys Gly Ala Thr
370                 375                 380

Phe Asn Arg Glu Thr Pro Gly Val Pro Ile Ala Tyr Thr Thr Asn Phe
385                 390                 395                 400

Leu Lys Asp Asn Glu Leu Ala Val Ile Lys Asn Asn Ser Glu Tyr Ile
                405                 410                 415

Glu Thr Thr Ser Lys Ala Tyr Thr Asp Gly Lys Ile Asn Ile Asp His
            420                 425                 430

Ser Gly Gly Tyr Val Ala Gln Phe Asn Ile Ser Trp Asp Glu Val Asn
        435                 440                 445

Tyr Asp Pro Glu Gly Asn Glu Ile Val Gln His Lys Asn Trp Ser Glu
450                 455                 460

Asn Asn Lys Ser Lys Leu Ala His Phe Thr Ser Ser Ile Tyr Leu Pro
465                 470                 475                 480

Gly Asn Ala Arg Asn Ile Asn Val Tyr Ala Lys Glu Cys Thr Gly Leu
                485                 490                 495

Ala Trp Glu Trp Trp Arg Thr Val Ile Asp Asp Arg Asn Leu Pro Leu
            500                 505                 510

Val Lys Asn Arg Asn Ile Ser Ile Trp Gly Thr Thr Leu Tyr Pro Lys
        515                 520                 525

Tyr Ser Asn Lys Leu Gln Val Asp Asn Pro Ile Glu
530                 535                 540

<210> SEQ ID NO 5
<211> LENGTH: 28
```

```
<212> TYPE: PRT
<213> ORGANISM: Listeria monocytogenes

<400> SEQUENCE: 5

Met Lys Lys Ile Met Leu Val Phe Ile Thr Leu Ile Leu Val Ser Leu
1               5                   10                  15

Pro Ile Ala Gln Gln Thr Glu Ala Lys Asp Ala Ser
            20                  25

<210> SEQ ID NO 6
<211> LENGTH: 84
<212> TYPE: DNA
<213> ORGANISM: Listeria monocytogenes

<400> SEQUENCE: 6
atgaaaaaaa taatgctagt ttttattaca cttatattag ttagtctacc aattgcgcaa      60
caaactgaag caaaggatgc atcg                                            84

<210> SEQ ID NO 7
<211> LENGTH: 84
<212> TYPE: DNA
<213> ORGANISM: Gallus gallus

<400> SEQUENCE: 7
gatgaagtct caggccttga gcagcttgag agtataatca actttgaaaa actgactgaa      60
tggaccagtt ctaatgttat ggaa                                            84

<210> SEQ ID NO 8
<211> LENGTH: 84
<212> TYPE: DNA
<213> ORGANISM: Gallus gallus

<400> SEQUENCE: 8
gatgaagtga gcggcctgga gcagctggag agcattatca acttcgaaaa actgaccgag      60
tggaccagca gcaatgtgat ggaa                                            84

<210> SEQ ID NO 9
<211> LENGTH: 28
<212> TYPE: PRT
<213> ORGANISM: Gallus gallus

<400> SEQUENCE: 9

Asp Glu Val Ser Gly Leu Glu Gln Leu Glu Ser Ile Ile Asn Phe Glu
1               5                   10                  15

Lys Leu Thr Glu Trp Thr Ser Ser Asn Val Met Glu
            20                  25

<210> SEQ ID NO 10
<211> LENGTH: 8
<212> TYPE: PRT
<213> ORGANISM: Gallus gallus

<400> SEQUENCE: 10

Ser Ile Ile Asn Phe Glu Lys Leu
1               5

<210> SEQ ID NO 11
<211> LENGTH: 24
<212> TYPE: DNA
<213> ORGANISM: Gallus gallus
```

```
<400> SEQUENCE: 11
agcatcatca acttcgagaa actg                                          24

<210> SEQ ID NO 12
<211> LENGTH: 24
<212> TYPE: DNA
<213> ORGANISM: Artificial Sequence
<220> FEATURE:
<223> OTHER INFORMATION: 5'-end homologous sequence

<400> SEQUENCE: 12
ccgaaatata gtaataaact gcag                                          24

<210> SEQ ID NO 13
<211> LENGTH: 24
<212> TYPE: DNA
<213> ORGANISM: Artificial Sequence
<220> FEATURE:
<223> OTHER INFORMATION: 3'-end homologous sequence

<400> SEQUENCE: 13
ctgcaggtag ataatccaat cgaa                                          24

<210> SEQ ID NO 14
<211> LENGTH: 10
<212> TYPE: PRT
<213> ORGANISM: Artificial Sequence
<220> FEATURE:
<223> OTHER INFORMATION: Linking sequence

<400> SEQUENCE: 14

Gly Gly Gly Gly Ser Gly Gly Gly Gly Ser
1               5                   10

<210> SEQ ID NO 15
<211> LENGTH: 28
<212> TYPE: PRT
<213> ORGANISM: Artificial Sequence
<220> FEATURE:
<223> OTHER INFORMATION: OVA8 with a linking sequence

<400> SEQUENCE: 15

Gly Gly Gly Gly Ser Gly Gly Gly Gly Ser Ser Ile Ile Asn Phe Glu
1               5                   10                  15

Lys Leu Gly Gly Gly Gly Ser Gly Gly Gly Gly Ser
            20                  25

<210> SEQ ID NO 16
<211> LENGTH: 48
<212> TYPE: PRT
<213> ORGANISM: Artificial Sequence
<220> FEATURE:
<223> OTHER INFORMATION: OVA28 with a linking sequence

<400> SEQUENCE: 16

Gly Gly Gly Gly Ser Gly Gly Gly Gly Ser Asp Glu Val Ser Gly Leu
1               5                   10                  15

Glu Gln Leu Glu Ser Ile Ile Asn Phe Glu Lys Leu Thr Glu Trp Thr
            20                  25                  30

Ser Ser Asn Val Met Glu Gly Gly Gly Gly Ser Gly Gly Gly Gly Ser
        35                  40                  45
```